(12) United States Patent
Morita et al.

(10) Patent No.: US 11,224,871 B2
(45) Date of Patent: Jan. 18, 2022

(54) PHOSPHATE ADSORBING AGENT FOR BLOOD PROCESSING, BLOOD PROCESSING SYSTEM AND BLOOD PROCESSING METHOD

(71) Applicant: ASAHI KASEI MEDICAL CO., LTD., Tokyo (JP)

(72) Inventors: Naoki Morita, Tokyo (JP); Hiroshi Tajima, Tokyo (JP); Masashi Kogawa, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 40 days.

(21) Appl. No.: 16/614,066

(22) PCT Filed: May 17, 2018

(86) PCT No.: PCT/JP2018/019077
§ 371 (c)(1),
(2) Date: Nov. 15, 2019

(87) PCT Pub. No.: WO2018/212269
PCT Pub. Date: Nov. 22, 2018

(65) Prior Publication Data
US 2020/0171479 A1   Jun. 4, 2020

(30) Foreign Application Priority Data
May 17, 2017   (JP) ................. JP2017-098444

(51) Int. Cl.
| B01J 47/014 | (2017.01) |
| A61M 1/16 | (2006.01) |
| B01J 41/13 | (2017.01) |
| B01D 15/36 | (2006.01) |
| B01J 41/02 | (2006.01) |
| B01J 41/04 | (2017.01) |
| B01J 41/10 | (2006.01) |
| B01J 41/14 | (2006.01) |
| B01J 47/04 | (2006.01) |

(52) U.S. Cl.
CPC .......... *B01J 47/014* (2017.01); *A61M 1/1621* (2014.02); *B01D 15/363* (2013.01); *B01J 41/02* (2013.01); *B01J 41/04* (2013.01); *B01J 41/10* (2013.01); *B01J 41/13* (2017.01); *B01J 41/14* (2013.01); *B01J 47/04* (2013.01)

(58) Field of Classification Search
CPC ......... B01J 20/06; B01J 47/014; B01J 41/02; B01J 41/04; B01J 41/09; B01J 41/10
See application file for complete search history.

(56) References Cited

U.S. PATENT DOCUMENTS

| 4,076,892 | A | 2/1978 | Fennimore et al. |
| 4,988,569 | A | 1/1991 | Okazaki et al. |
| 5,846,426 | A | 12/1998 | Boos et al. |
| 2002/0197252 | A1 | 12/2002 | Brady et al. |
| 2007/0093739 | A1 | 4/2007 | Brady et al. |
| 2007/0128424 | A1* | 6/2007 | Omori ............... B01J 20/06 428/304.4 |
| 2008/0154007 | A1* | 6/2008 | Mori ................. B01J 20/26 526/328.5 |
| 2008/0213523 | A1 | 9/2008 | Fujimoto et al. |
| 2008/0317701 | A1 | 12/2008 | Koike et al. |
| 2012/0219799 | A1 | 8/2012 | Omori |
| 2013/0288007 | A1* | 10/2013 | Wang ................ C04B 35/624 428/156 |
| 2017/0333871 | A1 | 11/2017 | Fujieda et al. |
| 2018/0326136 | A1 | 11/2018 | Morita et al. |
| 2018/0369781 | A1 | 12/2018 | Omori et al. |

FOREIGN PATENT DOCUMENTS

| CN | 101198549 A | 6/2008 |
| EP | 3375465 | 9/2018 |
| JP | 60-132644 | 7/1985 |
| JP | 1986-004529 A | 1/1986 |
| JP | 01-056141 | 3/1989 |
| JP | 2002-102335 | 4/2002 |
| JP | 3406360 B2 | 5/2003 |
| JP | 2004-305915 | 11/2004 |
| JP | 2005-514127 | 5/2005 |
| JP | 2006-320729 A | 11/2006 |
| JP | 2006-346542 | 12/2006 |
| JP | 2007-054509 A | 3/2007 |
| JP | 2010-106071 | 5/2010 |

(Continued)

OTHER PUBLICATIONS

Tanaka et al. "Blood compatible aspects of poly(2-methoxyethylacrylate) (PMEA)-relationship between protein adsorption and platelet adhesion on PMEA surface" (Biomaterials 21, 2000, p. 1471-1481) (Year: 2000).*

Ye et al. "Optimizing spatial pore-size and porosity distributions of adsorbents for enhanced adsorption and desorption performance" (Chemical Engineering Science, 132, 2015, p. 108-117) (Year: 2015).*

(Continued)

*Primary Examiner* — Ryan B Huang
(74) *Attorney, Agent, or Firm* — Greenblum & Bernstein, P.L.C.

(57) ABSTRACT

The present invention provides a phosphate adsorbing agent for blood processing comprising a porous formed article comprising an organic polymer resin and an inorganic ion adsorbent and having a most frequent pore size of 0.08 to 0.70 μm measured with a mercury porosimeter, the phosphate adsorbing agent for blood processing having a biocompatible polymer in the surface of the porous formed article.

15 Claims, 25 Drawing Sheets

(56) References Cited

FOREIGN PATENT DOCUMENTS

| | | |
|---|---|---|
| JP | 2010-227757 | 10/2010 |
| JP | 4671419 | 1/2011 |
| JP | 2017-104853 A | 6/2017 |
| WO | 2002/015964 | 2/2002 |
| WO | 2005/056175 A1 | 6/2005 |
| WO | 2006/038603 | 4/2006 |
| WO | 2011/062277 | 5/2011 |
| WO | 2011/125758 | 10/2011 |
| WO | 2016/067967 A | 5/2016 |
| WO | 2017/082423 | 5/2017 |

OTHER PUBLICATIONS

Masaru Tanaka, Material Biocompatibilizing Surface of Artificial Organ, Bio Industry, vol. 20, No. 12, 59-70 2003, with partial English translation.

International Search Report issued in International Patent Application No. PCT/JP2018/019077, dated Jul. 17, 2018, in English.

International Preliminary Report on Patentability, issued in International Patent Application No. PCT/JP2018/019077, dated Nov. 19, 2019, in English.

European Search Report, European Patent Office, Application No. 18801879.0, dated Apr. 5, 2020.

Tanaka et al., "Blood compatible aspects of poly(2-methoxyethylacrylate) (PMEA)—relationship between protein adsorption and platelet adhesion on PMEA surface", Biomaterials, vol. 21, No. 14, Jul. 2000, pp. 1471-1481, XP004199068, ISSN: 0142-9612, DOI: 10.1016/S0142-9612(00)0031-4.

Restriction Requirement dated Jan. 7, 2021 in U.S. Appl. No. 15/775,048 which published as US 2018-0369781 A1.

Non-Final Office Action dated May 13, 2021 in U.S. Appl. No. 15/775,048.

Notices of Allowance and Allowability dated Sep. 10, 2021 in U.S. Appl. No. 15/775,048.

Restriction Requirement dated May 1, 2020 in U.S. Appl. No. 15/774,858 which published as US 2018/0326136 A1 and is a national stage of PCT/JP2016/083605 which published as WO 2017/082423 A1 (each cited in Information Disclosure Statement filed Feb. 19, 2020).

Restriction Requirement dated Sep. 18, 2020 in U.S. Appl. No. 15/774,858.

Non-Final Office Action dated Jan. 22, 2021 in U.S. Appl. No. 15/774,858.

Final Office Action dated Jul. 22, 2021 in U.S. Appl. No. 15/774,858.

Yutaka Kanai (2011), Study on the analysis of colloidal materials by ultrafiltration method (Study on elucidation and characterization of colloid (part 3)), Bull. Geol. Surv. Japan, vol. 62 (9/10), pp. 371-388, 14 figs., 1 table.

\* cited by examiner

[Figure 18]
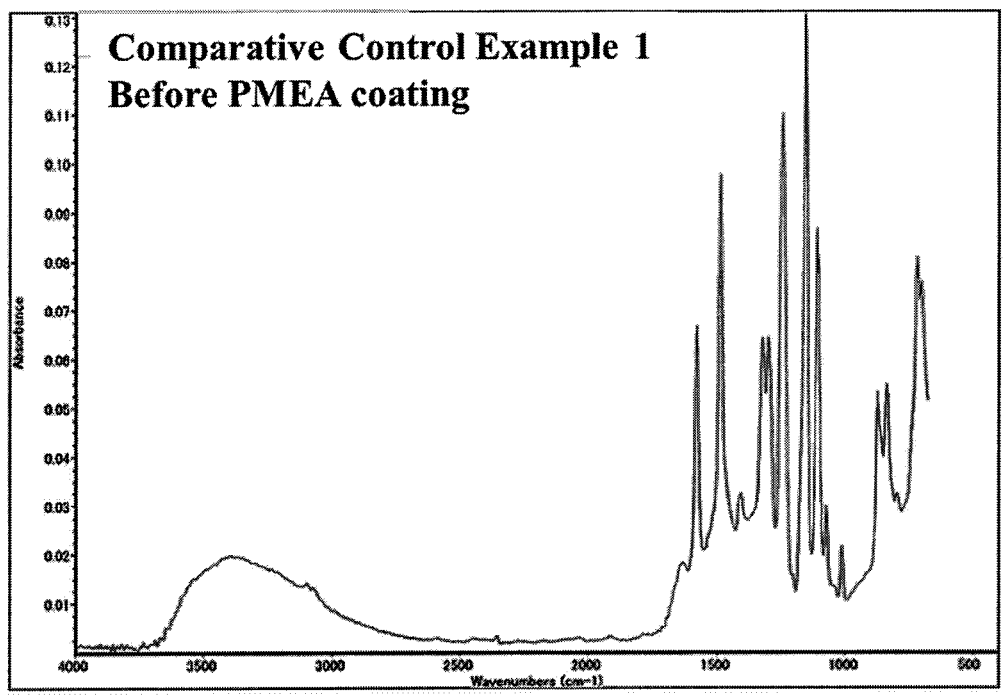
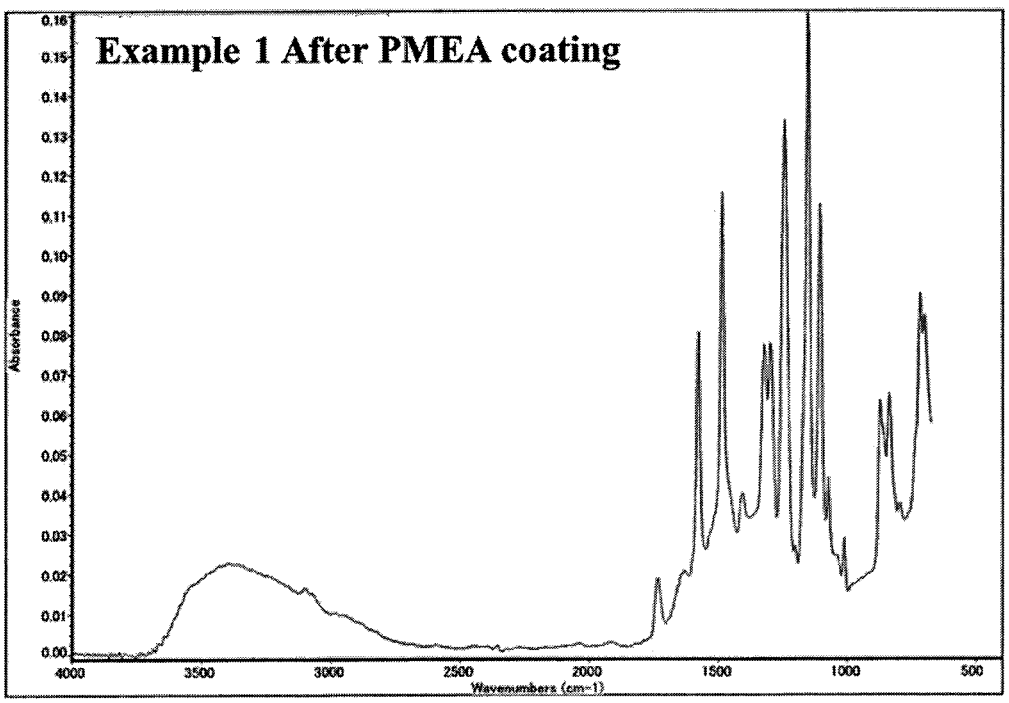

[Figure 19]
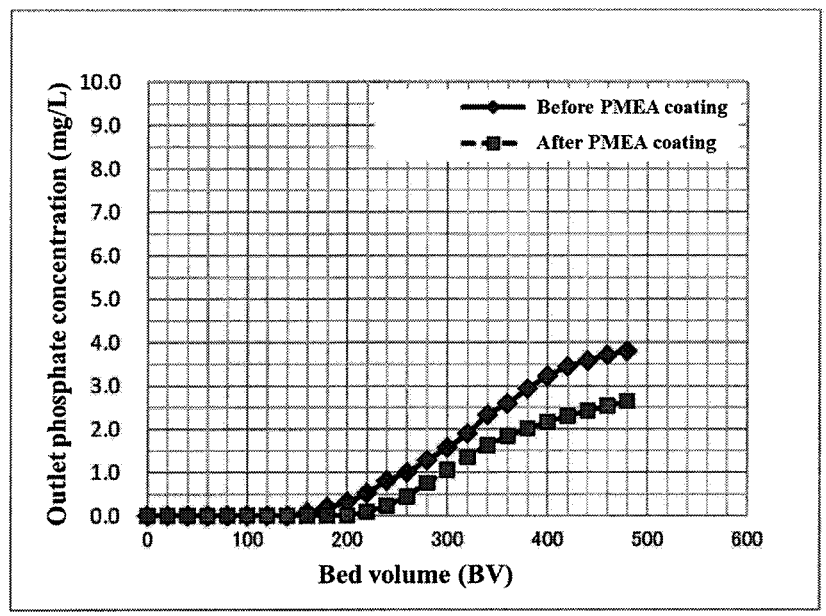

[Figure 20]
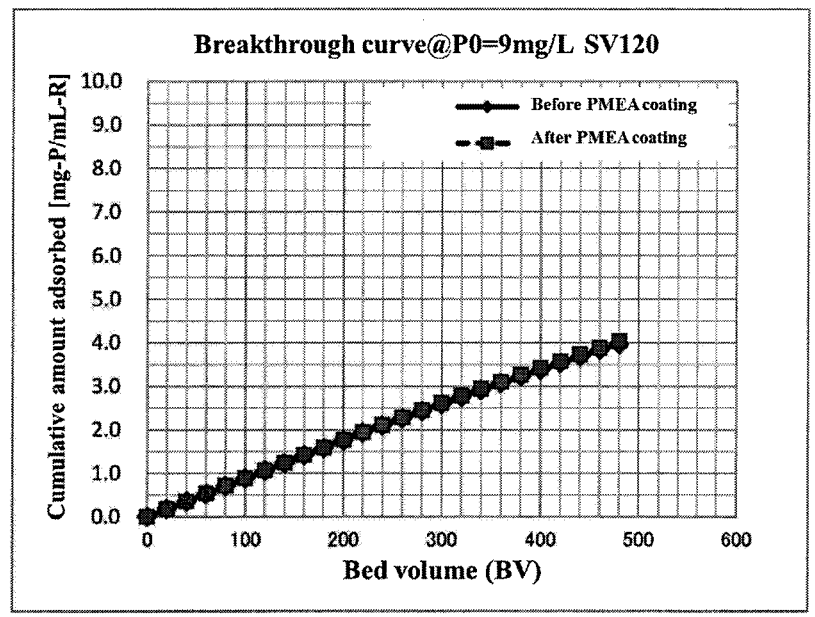

[Figure 21]
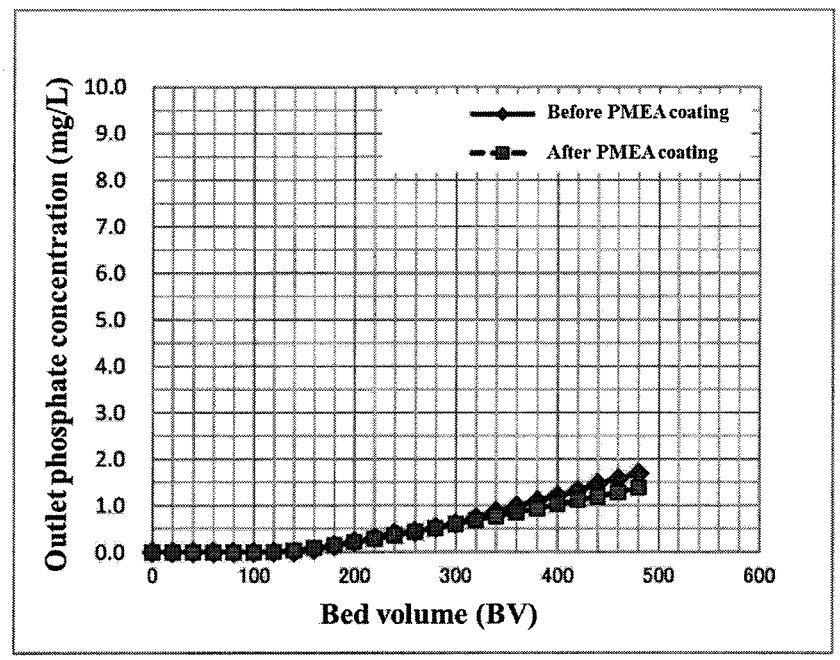

[Figure 22]
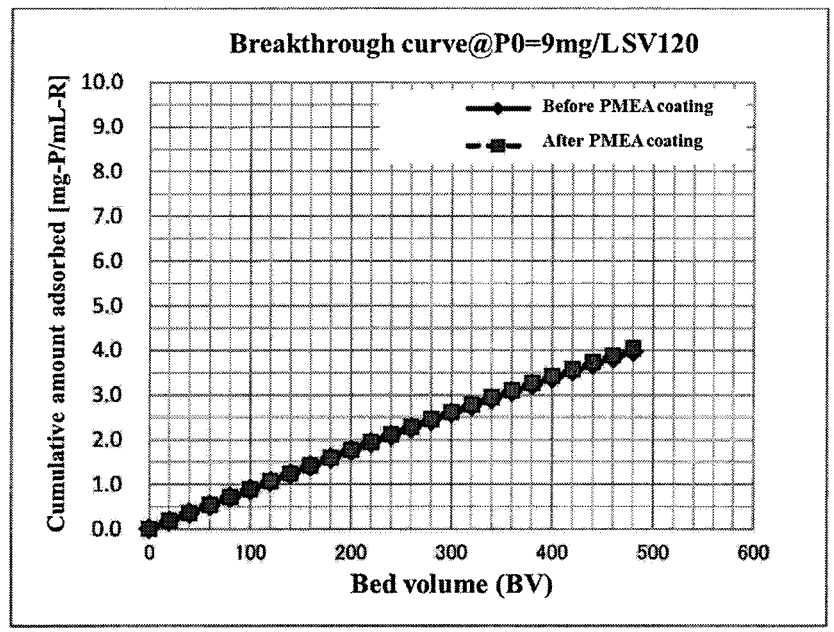

[Figure 23]
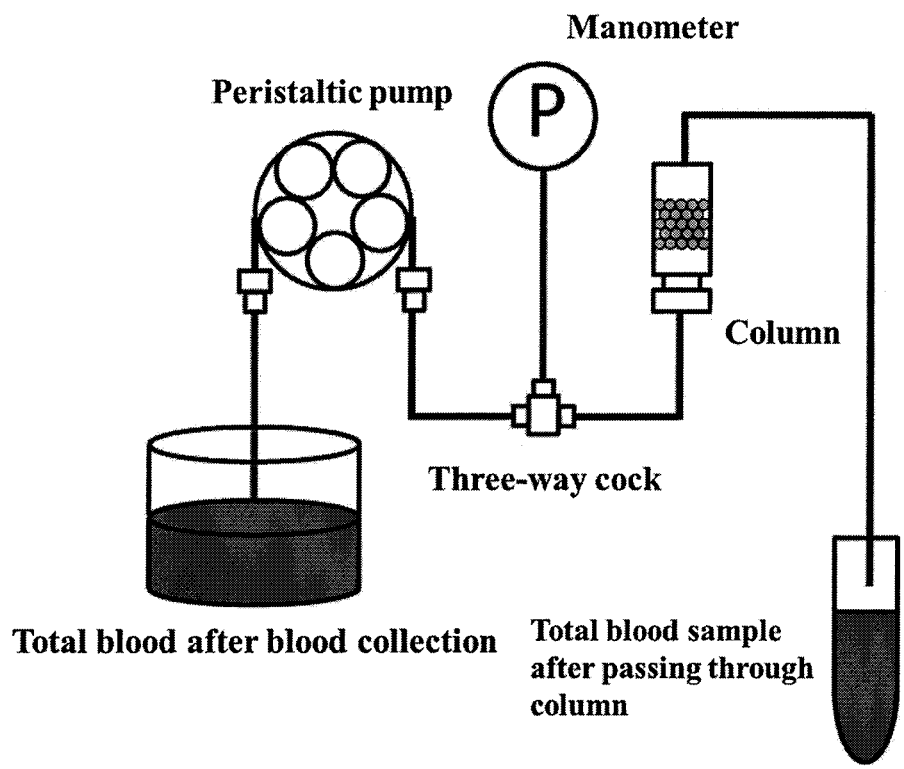

[Figure 24]
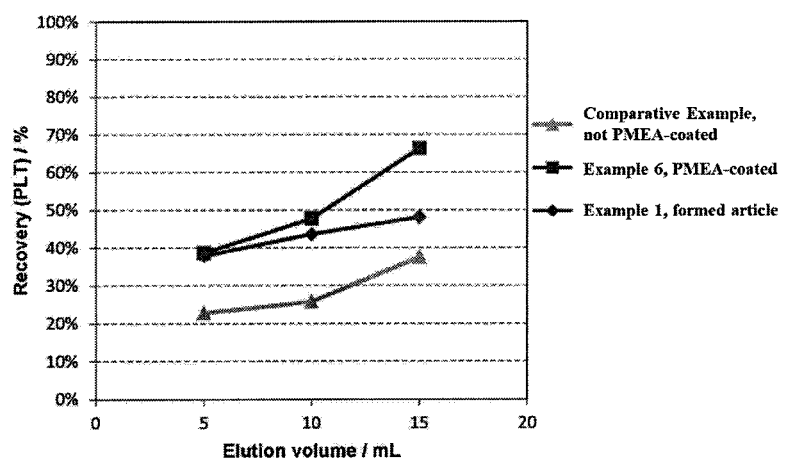

[Figure 25]
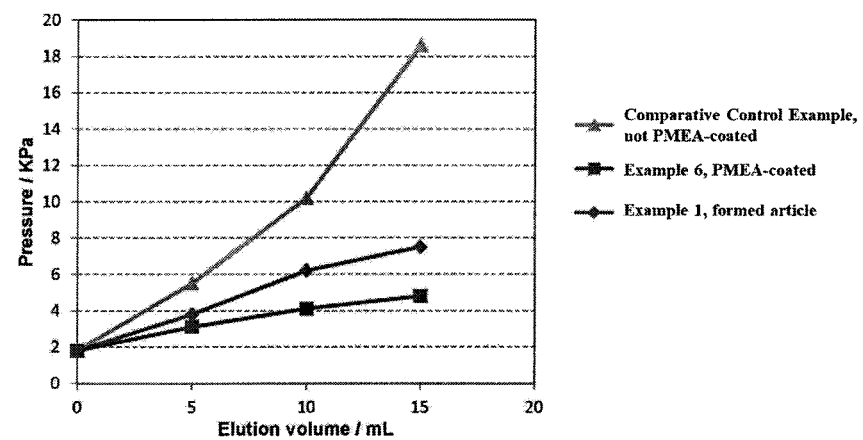

PHOSPHATE ADSORBING AGENT FOR BLOOD PROCESSING, BLOOD PROCESSING SYSTEM AND BLOOD PROCESSING METHOD

TECHNICAL FIELD

The present invention relates to a phosphate adsorbing agent for blood processing and a blood processing system. The present invention further relates to a blood processing method using the phosphate adsorbing agent for blood processing.

BACKGROUND ART

In healthy adults whose kidney functions normally, excessive phosphate in the body is excreted mainly as urine from the body. On the other hand, for example, kidney disease patients, such as chronic renal failure patients, who have impaired renal functions cannot properly excrete excessive phosphate from their bodies. Therefore, phosphate accumulates gradually in the body, causing a disease such as hyperphosphatemia.

Sustained hyperphosphatemia causes secondary hyperparathyroidism which results in renal bone disease characterized by symptoms such as painful bone, fragile bone, bone deformation, and susceptibility to fracture. Such renal bone disease complicated with hypercalcemia increases the risk of developing heart failure due to cardiovascular calcification.

The cardiovascular calcification is one of the most serious complications of chronic renal failure and the like. Therefore, for chronic renal failure patients, it is very important to properly control the amount of phosphate in the body in order to prevent hyperphosphatemia.

In hemodialysis patients, phosphate accumulated in the body is regularly removed and controlled by dialysis therapy such as hemodialysis, hemodiafiltration and hemofiltration so as not to cause hyperphosphatemia. The dialysis therapy generally requires three times a week and a treatment time of 4 hours each time.

However, if hemodialysis patients ingest 1000 mg of phosphate, which is a daily intake for healthy adult humans, phosphate (650 mg) supposed to be excreted from the kidney accumulates in the body and accumulates at a level as large as 4550 mg in 1 week. Ordinary hemodialysis is capable of removing phosphate on the order of 800 to 1000 mg by one treatment of dialysis and is capable of removing approximately 3000 mg of phosphate by dialysis three times a week. The amount (3000 mg) of phosphate that can be removed by dialysis therapy falls short of the amount (4550 mg) of phosphate accumulated in 1 week. As a result, phosphate accumulates in the body.

Among others, maintenance dialysis patients who are chronic renal failure patients lack renal functions serving as the main elimination route of phosphate and therefore substantially lack the function of excreting phosphate into urine. In dialysis therapy, phosphate can be removed from the body through a diffusion event into a dialysis fluid because the dialysis fluid is free from phosphate. In fact, sufficient excretion cannot be achieved by current dialysis time and dialysis conditions.

As mentioned above, the dialysis therapy alone is not sufficiently effective for removing phosphate. Therefore, in addition to the dialysis therapy, diet therapy and drug therapy based on the drinking of phosphate adsorbing agents are carried out in order to control phosphate. The important thing is to limit phosphate intakes after confirmation that patients are not nutritionally depleted by the evaluation of their nutritional conditions.

For phosphate control, the CKD-MBD (Chronic Kidney Disease-Mineral and Bone Disorder) guideline reports that serum phosphate levels are 3.5 to 6.0 mg/dL.

A serum phosphate level of 3.5 mg/dL or lower is hypophosphatemia and is responsible for rachitis or osteomalacia, whereas a serum phosphate level of 6.0 mg/dL or higher is hyperphosphatemia and is responsible for cardiovascular calcification.

The diet therapy which involves reducing phosphate intakes depends on the nutritional conditions of patients and must also take patients' own tastes into consideration. Therefore, it is difficult to control phosphate concentrations in the body by the diet therapy.

In the drug therapy, phosphate concentrations are controlled by the administration before or during each meal of an oral phosphate adsorbing agent which forms insoluble phosphate through binding to food-derived phosphate ions in the gastrointestinal tract and thereby suppresses the absorption of phosphate from the intestinal tract. In the drug therapy, however, the amount of the phosphate adsorbing agent drunk at the time of each meal is considerably large. Therefore, vomiting, a feeling of fullness, constipation, accumulation of the drug in the body, etc. occur with high probability as adverse reactions of the administered phosphate adsorbing agent. Therefore, drug compliance is very low (reportedly 50% or less) due to these adverse reactions. Thus, it is difficult both for doctors and for patients to control phosphate concentrations by use of the drug.

Patent Literature 1 discloses that phosphate in blood is efficiently removed without the direct contact of a phosphate adsorbing agent with blood, by circulating a dialysis composition comprising a phosphate adsorbing agent in a dialysis fluid at the time of hemodialysis treatment.

Patent Literature 2 discloses a hemodialysis system in which a phosphate adsorbing agent which removes phosphate accumulated in blood is disposed, aside from a hemodialyzer, in an extracorporeal blood circuit.

Patent Literature 3 discloses a porous formed article suitable for an adsorbing agent which can remove phosphate and the like by adsorption at a high speed.

CITATION LIST

Patent Literature

Patent Literature 1: International Publication No. WO 2011/125758
Patent Literature 2: Japanese Patent Laid-Open No. 2002-102335
Patent Literature 3: Japanese Patent No. 4671419

SUMMARY OF INVENTION

Technical Problem

However, the system disclosed in Patent Literature 1 has the difficulty in completely eliminating phosphate on a concentration gradient. Furthermore, it is considered that the effect of eliminating phosphate is decreased because the concentration gradient of phosphate is decreased with increase in the performance of a dialysis membrane. In terms of the properties of dialysis fluid composition, there is also the possibility that insoluble matter remains. Thus, it may become difficult to control water system piping during dialysis.

In the system disclosed in Patent Literature 2, phosphate is adsorbed by exchange with hydrochloride in a polycationic polymer disclosed as a phosphate adsorbing agent so that the hydrochloride is eliminated. For this reason and due to the presence of calcium-containing matter or an active carbon portion, actual use of the system might cause harmful effects (adverse reactions, etc.) associated with the performance of a phosphate adsorbing portion, biocompatibility and safety, etc.

Patent Literature 3 disclosing the porous formed article makes no mention about phosphate in blood in the body. Thus, further studies are demanded.

An object of the present invention is to provide a porous formed article that can properly control phosphate concentrations in blood in the body.

Solution to Problem

The present inventors have conducted diligent studies to solve the problems described above and consequently completed the present invention by finding that the problems described above can be solved by using, as a phosphate adsorbing agent for blood processing, a porous formed article comprising an organic polymer resin and an inorganic ion adsorbent, having a most frequent pore size within a specific range measured with a mercury porosimeter, and having a biocompatible polymer in the surface thereof.

Advantageous Effects of Invention

The present invention can provide a porous formed article that can properly control phosphate concentrations in blood in the body.

BRIEF DESCRIPTION OF DRAWINGS

FIG. 18 shows infrared absorption curves of the porous formed articles prepared in Example 1 and Comparative Control Example 1.

FIG. 19 shows results of measuring an outlet phosphate concentration over time using a phosphate measurement apparatus Phosphax Compact (trade name) manufactured by HACH Company for the porous formed articles prepared in Example 1 and Comparative Control Example 1.

FIG. 20 shows a cumulative amount adsorbed measured using a phosphate measurement apparatus Phosphax Compact (trade name) manufactured by HACH Company for the porous formed articles prepared in Example 1 and Comparative Control Example 1.

FIG. 21 shows results of measuring an outlet phosphate concentration over time using a phosphate measurement apparatus Phosphax Compact (trade name) manufactured by HACH Company for porous formed articles prepared in Example 2 and Comparative Control Example 2.

FIG. 22 shows a cumulative amount adsorbed measured using a phosphate measurement apparatus Phosphax Compact (trade name) manufactured by HACH Company for the porous formed articles prepared in Example 2 and Comparative Control Example 2.

FIG. 23 shows a schematic diagram of a circuit for a blood compatibility evaluation test using human blood in Example 6 and Comparative Control Example 6.

FIG. 24 shows results of measuring a platelet count (PLT) for porous formed articles prepared in Example 1, and Example 6 and Comparative Control Example 6.

FIG. 25 shows change in pressure (KPa) measured in a manometer for the porous formed articles prepared in Example 1, and Example 6 and Comparative Control Example 6.

DESCRIPTION OF EMBODIMENTS

Figure 1:
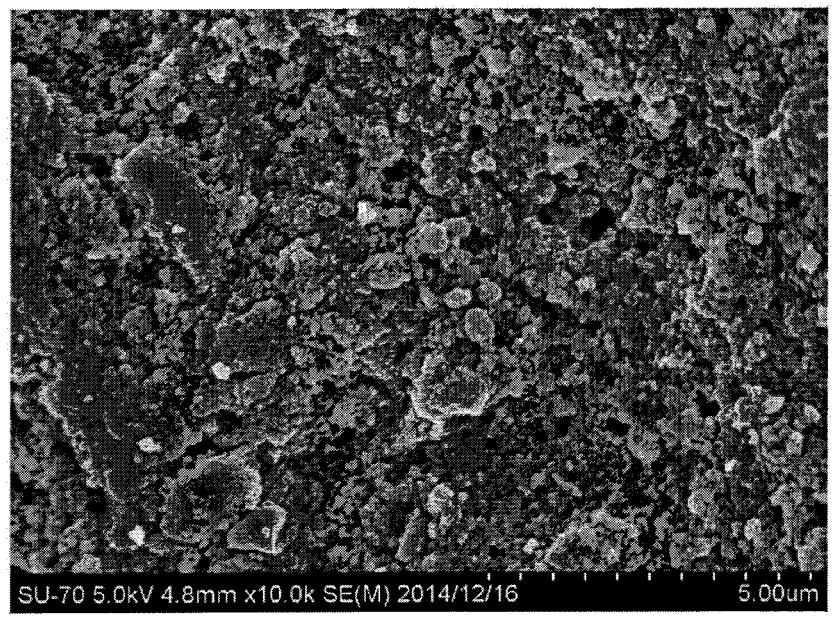
FIG. 1 shows an electron microscope photograph (magnification: ×10,000) showing the outer surface of a porous formed article obtained in Production Example 1.
Figure 2:
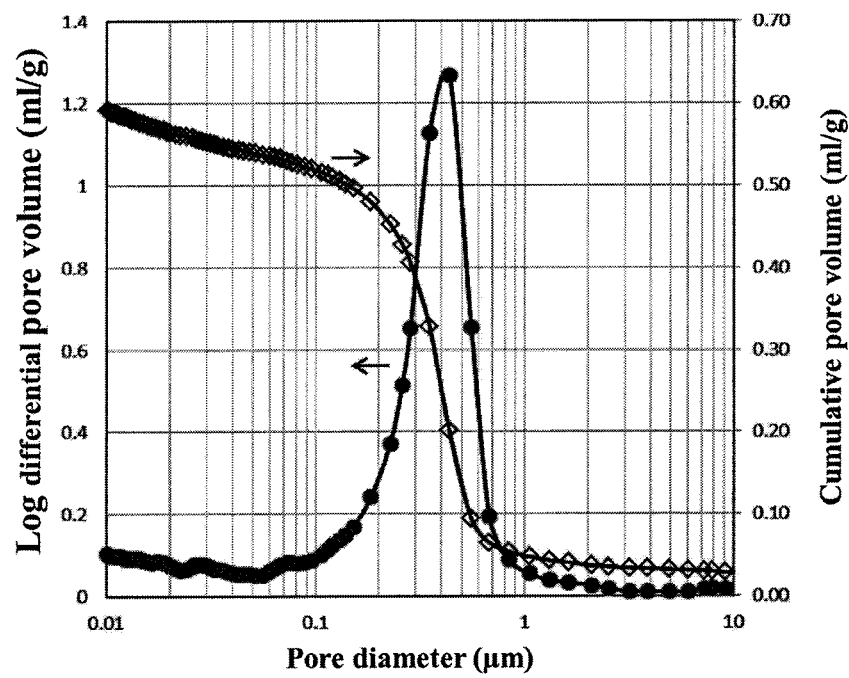
FIG. 2 shows the pore distribution diagram of the porous formed article obtained in Production Example 1, wherein a log differential pore volume and a cumulative pore volume were plotted against a pore diameter measured with a mercury porosimeter.
Figure 3:
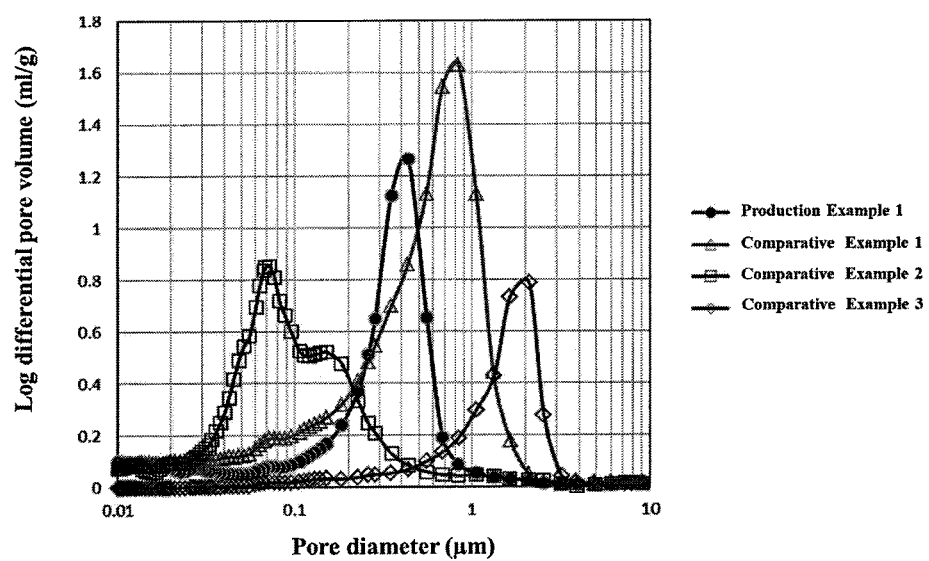
FIG. 3 shows the pore distribution diagram of porous formed articles obtained in Production Example 1 and Comparative Examples 1, 2 and 3, wherein a log differential pore volume was plotted against a pore diameter measured with a mercury porosimeter.
Figure 4:
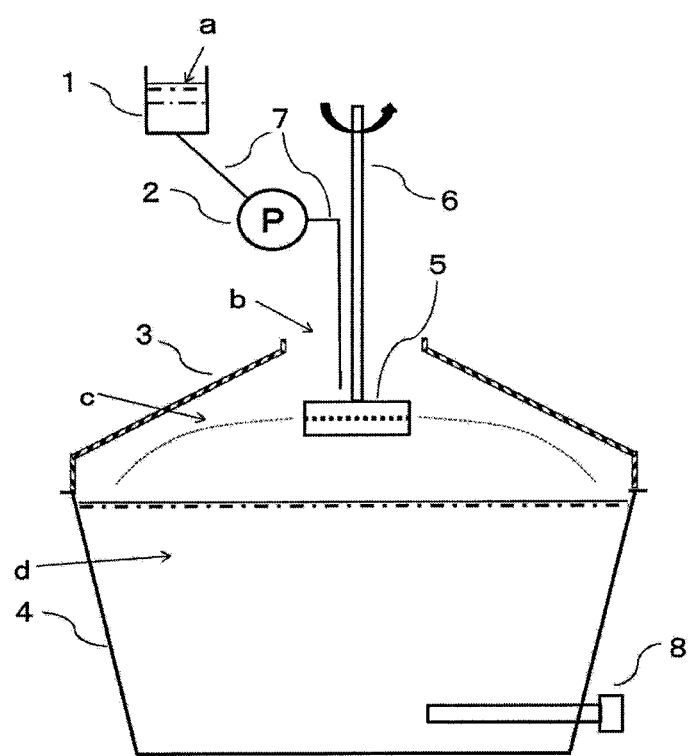
FIG. 4 is a schematic diagram showing a production apparatus for the porous formed article according to the present embodiment.

Hereinafter, the mode for carrying out the present invention (hereinafter, referred to as the "present embodiment") will be described in detail. However, the present invention is not limited by the embodiments described below, and various changes or modifications can be made therein without departing from the scope of the present invention.
(Phosphate Adsorbing Agent for Blood Processing)

The phosphate adsorbing agent for blood processing of the present embodiment comprises a porous formed article. The porous formed article comprises an organic polymer resin and an inorganic ion adsorbent and has a most frequent pore size of 0.08 to 0.70 μm measured with a mercury porosimeter. In the phosphate adsorbing agent for blood processing of the present embodiment, the porous formed article has a biocompatible polymer in the surface thereof.

The porous formed article has continuous holes and has a porous structure.

The phosphate adsorbing agent for blood processing of the present embodiment is excellent in selectivity and adsorbing properties for phosphate in blood even at a high blood flow rate at the time of treatment with extracorporeal circulation, and can eliminate a necessary amount of phosphate in blood without influencing other components in the blood. Furthermore, the phosphate adsorbing agent for blood processing can properly control phosphate concentrations in blood without the drinking of oral phosphate adsorbing agents or the like having adverse reactions, because phosphate in the blood can be effectively removed by extracorporeal circulation. Moreover, the phosphate adsorbing agent for blood processing can efficiently excrete phosphate from the body by combined use with hemodialysis treatment, because the phosphate adsorbing agent can be effectively used even at the time of treatment with extracorporeal circulation having a high blood flow rate.

Thus, use of the phosphate adsorbing agent for blood processing of the present embodiment can properly control phosphate concentrations in blood in the body without causing adverse reactions in dialysis patients even if the dialysis patients take no oral phosphate adsorbing agent or take only a small amount of an oral phosphate adsorbing agent (auxiliary use).

The porous formed article according to the present embodiment has a most frequent pore size of 0.08 to 0.70 μm, preferably 0.10 to 0.60 μm, more preferably 0.12 to 0.60 μm, further preferably 0.12 to 0.50 μm, still further preferably 0.20 to 0.50 μm, measured with a mercury porosimeter.

In the present embodiment, the most frequent pore size (most frequent diameter) means a pore diameter that exhibits the largest value of a log differential pore volume on a diagram in which the log differential pore volume (dV/d (log D), wherein V represents a mercury penetration volume, and D represents a pore diameter) is plotted against the pore diameter measured with a mercury porosimeter, and is based on a volume. Specifically, the most frequent pore size can be measured by a method described in Examples.

The mercury porosimeter is an apparatus for evaluating the sizes of pores in porous materials according to the mercury penetration method, and is suitable for the measurement of relatively large pore distributions (mesopores (several nm) to macropores (several hundreds of μm)) which cannot be measured by the gas adsorption method (BET method).

In the present embodiment, the most frequent pore size can be measured with the mercury porosimeter to thereby measure the detailed features of the porous structure (skeletal structure) consisting of the organic polymer resin in the porous formed article. Also, a median size and a specific surface area can be measured with the mercury porosimeter to thereby measure the detailed features of the porous structure (skeletal structure) consisting of the organic polymer resin in the porous formed article.

The most frequent pore size of 0.08 μm or larger is sufficient as the pore size of continuous holes for diffusing phosphate serving as an object to be adsorbed into the inside of the porous formed article, and accelerates a diffusion rate. The most frequent pore size of 0.70 μm or smaller is suitable for adsorbing many ions at the time of high-speed flushing because voids in the porous formed article are decreased so that the abundance of the inorganic ion adsorbent per unit volume is dense.

The outer surface opening ratio of the porous formed article is preferably 5% or more and less than 30%, more preferably 7% or more and 28% or less, further preferably 10% or more and 25% or less.

In the present embodiment, the outer surface opening ratio means the ratio of the total opening area of all holes to the area of a viewing field when the outer surface of the porous formed article is observed under a scanning electron microscope.

The outer surface opening ratio of 5% more accelerates the diffusion rate of phosphate serving as an object to be adsorbed into the inside of the porous formed article. The outer surface opening ratio of less than 30% allows ions in water to be reliably adsorbed even in high-speed fluid flow because the abundance of the inorganic ion adsorbent on the outer surface of the porous formed article is large.

In the present embodiment, the outer surface opening ratio is actually measured by observing the outer surface of the porous formed article at ×10,000. Specifically, the outer surface opening ratio can be measured by a method described in Examples.

The ratio of the most frequent pore size to a median size (most frequent pore size/median size) measured with a mercury porosimeter, of the porous formed article according to the present embodiment is preferably 0.80 to 1.30, more preferably 0.85 to 1.25, further preferably 0.90 to 1.20.

In the present embodiment, the median size means a pore diameter corresponding to a median value in the range from the largest value to the smallest value of cumulative pore volumes in a cumulative pore volume distribution, and is based on a volume. Specifically, the median size can be measured by a method described in Examples.

A most frequent pore size/median size ratio close to 1.0 is suitable for high-speed flushing because of the uniform pore size distribution of the porous formed article.

When a dense layer having a small pore size (skin layer) is present in the vicinity of the outer surface of the porous formed article, large voids (layer with the largest pore size) are easily formed on the inner side (inside direction of the formed article) of the skin layer. The most frequent pore size/median size ratio of 0.80 to 1.30 means that the skin layer is absent in the porous formed article.

The specific surface area measured with a mercury porosimeter, of the porous formed article according to the present embodiment is preferably 10 to 100 $m^2/cm^3$, more preferably 11 to 90 $m^2/cm^3$, further preferably 12 to 50 $m^2/cm^3$.

The specific surface area of 10 m²/cm³ or larger produces sufficient adsorption performance at the time of high-speed flushing because the amount of the inorganic ion adsorbent carried is large and the pore surface area is large. The specific surface area of 100 m²/cm³ or smaller produces the high strength of the porous formed article because the inorganic ion adsorbent is firmly carried.

In the present embodiment, the specific surface area is defined according to the following expression: Specific surface area (m²/cm³)=S(Hg) (m²/g)×Bulk specific gravity (g/cm³)

S(Hg) means the pore surface area (m²/g) per unit weight of the porous formed article. A method for measuring the pore surface area involves drying the porous formed article in vacuum at room temperature, followed by measurement using a mercury porosimeter. Specifically, the pore surface area can be measured by a method described in Examples.

A method for measuring the bulk specific gravity is as follows.

When the porous formed article is in the form of particles, a cylinder, a hollow cylinder or the like and is short in shape, the apparent volume of the porous formed article in a wet state is measured with 1 mL regarded as 1 cm³ using a measuring cylinder or the like. Then, the porous formed article is dried in vacuum at room temperature, and its weight is determined. The bulk specific gravity is calculated according to weight/volume.

When the porous formed article is in the form of a thread, a hollow fiber, a sheet or the like and is long in shape, the cross-section area and length of the wet porous formed article are measured. The volume is calculated from the product thereof. Then, the porous formed article is dried in vacuum at room temperature, and its weight is determined. The bulk specific gravity is calculated according to weight/volume.

The porous formed article according to the present embodiment is preferably substantially spherical with an average particle size of 100 to 2500 μm. The average particle size is more preferably 150 to 2000 μm, further preferably 200 to 1500 μm.

The porous formed article according to the present embodiment is preferably spherical particles. The spherical particles may be true spheres or oval spheres.

The average particle size of 100 μm or larger is suitable for high-speed flushing because pressure drop is small when a column, a tank or the like is packed with the porous formed article. The average particle size of 2500 μm or smaller allows ions to be reliably adsorbed even in high-speed fluid flow because the surface area can be large when a column or a tank is packed with the porous formed article.

In the present embodiment, the average particle size means a median size of a sphere-equivalent diameter determined from the angle distribution of scattered light intensity of laser light diffraction when the porous formed article is regarded as a sphere. Specifically, the average particle size can be measured by a method described in Examples.

(Organic Polymer Resin)

The organic polymer resin constituting the porous formed article according to the present embodiment is not particularly limited and is preferably a resin that can be rendered porous by an approach based on wet phase separation.

Examples of the organic polymer resin include polysulfone polymers, polyvinylidene fluoride polymers, polyvinylidene chloride polymers, acrylonitrile polymers, polymethyl methacrylate polymers, polyamide polymers, polyimide polymers, cellulose polymers, ethylene vinyl alcohol copolymer-based polymers and many types.

Among them, an ethylene vinyl alcohol copolymer (EVOH), polyacrylonitrile (PAN), polysulfone (PS), polyethersulfone (PES) and polyvinylidene fluoride (PVDF) are preferred because of non-swellability in water, biodegradation resistance, and easy production.

The organic polymer resin is preferably polyethersulfone terminally having a hydroxy group. The organic polymer resin having a hydroxy group as a terminal group can exert excellent carrying performance for the inorganic ion adsorbent in the porous formed article according to the present embodiment. In addition, the highly hydrophobic organic polymer resin is improved in hydrophilicity because of terminally having a hydroxy group, and is less likely to cause fouling in the porous formed article.

(Inorganic Ion Adsorbent)

The inorganic ion adsorbent constituting the porous formed article according to the present embodiment means an inorganic substance that exhibits an ion adsorption event or an ion exchange event.

Examples of the inorganic ion adsorbent of natural origin include various mineral substances such as zeolite and montmorillonite.

Specific examples of the various mineral substances include kaolin mineral having a single-layer lattice of aluminosilicate, muscovite having a two-layer lattice structure, glauconite, Kanuma soil, pyrophyllite, talc, feldspar having a three-dimensional skeletal structure, zeolite and montmorillonite.

Examples of the inorganic ion adsorbent of synthetic origin include metal oxides, salts of polyvalent metals and insoluble aqueous oxides. The metal oxides include mixed metal oxides, mixed metal hydroxides and aqueous oxides of metals.

The inorganic ion adsorbent preferably contains a metal oxide represented by the following formula (I) from the viewpoint of adsorption performance for an object to be adsorbed, particularly, phosphate:

$$MN_xO_n \cdot mH_2O \qquad (I)$$

In the formula (I), x is 0 to 3, n is 1 to 4, m is 0 to 6, and M and N are different from each other and each represent a metal element selected from the group consisting of Ti, Zr, Sn, Sc, Y, La, Ce, Pr, Nd, Sm, Eu, Gd, Tb, Dy, Ho, Er, Tm, Yb, Lu, Al, Si, Cr, Co, Ga, Fe, Mn, Ni, V, Ge, Nb and Ta.

The metal oxide may be a non-aqueous (non-hydrous) metal oxide represented by the formula (I) wherein m is 0, or may be an aqueous metal oxide (hydrous metal oxide) represented by the formula (I) wherein m is a numerical value other than 0.

The metal oxide represented by the formula (I) wherein x is a numerical value other than 0 is a mixed metal oxide in which each metal element contained is uniformly distributed with regularity throughout the oxide and the compositional ratio of metal elements contained in the metal oxide is represented by a fixed chemical formula.

Specifically, such a metal oxide forms a perovskite structure, a spinel structure or the like, and examples thereof include nickel ferrite ($NiFe_2O_4$) and aqueous ferrite of zirconium $Zr \cdot Fe_2O_4 \cdot mH_2O$, wherein m is 0.5 to 6).

The inorganic ion adsorbent may contain a plurality of metal oxides represented by the formula (I).

The inorganic ion adsorbent preferably contains at least one material selected from any of the following groups (a) to (c) from the viewpoint of excellent adsorption performance for an object to be adsorbed, particularly, phosphate:

(a) hydrous titanium oxide, hydrous zirconium oxide, hydrous tin oxide, hydrous cerium oxide, hydrous lanthanum oxide and hydrous yttrium oxide,
(b) a mixed metal oxide of at least one metal element selected from the group consisting of titanium, zirconium, tin, cerium, lanthanum and yttrium, and at least one metal element selected from the group consisting of aluminum, silicon and iron, and
(c) activated alumina.

A material selected from any of the groups (a) to (c) may be used, materials selected from any of the groups (a) to (c) may be used in combination, or the respective materials of the groups (a) to (c) may be used in combination. For the combined use, a mixture of two or more materials selected from any of the groups (a) to (c) may be used, or a mixture of two or more materials selected from two or more of the groups (a) to (c) may be used.

The inorganic ion adsorbent may contain aluminum sulfate-impregnated activated alumina from the viewpoint of inexpensiveness and high adsorbing properties.

In addition to the metal oxide represented by the formula (I), it is more preferred for the inorganic ion adsorbent to further solid-dissolve a metal element other than M and N, from the viewpoint of inorganic ion adsorbing properties and production cost.

Examples thereof include iron solid-dissolved in hydrous zirconium oxide represented by $ZrO_2 \cdot mH_2O$ (m is a numerical value other than 0).

Examples of the salts of polyvalent metals include a hydrotalcite compound represented by the following formula (II):

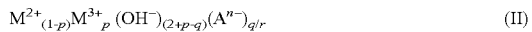

$$M^{2+}_{(1-p)}M^{3+}_{p}(OH^-)_{(2+p-q)}(A^{n-})_{q/r} \qquad (II)$$

In the formula (II), $M^{2+}$ is at least one divalent metal ion selected from the group consisting of $Mg^{2+}$, $Ni^{2+}$, $Zn^{2+}$, $Fe^{2+}$, $Ca^{2+}$ and $Cu^{2+}$.

$M^{3+}$ is at least one trivalent metal ion selected from the group consisting of $Al^{3+}$ and $Fe^{3+}$.

$A^{n-}$ is a n-valent anion.

p is $0.1 \leq p \leq 0.5$, q is $0.1 \leq q \leq 0.5$, and r is 1 or 2.

The hydrotalcite compound represented by the formula (II) is preferred because of an inexpensive raw material and high adsorbing properties as the inorganic ion adsorbent.

Examples of the insoluble aqueous oxides include insoluble heteropoly acid salts and insoluble hexacyanoferrate.

The inorganic ion adsorbent constituting the porous formed article according to the present embodiment may contain a contaminating impurity element ascribable to a production method thereof, etc., without inhibiting the functions of the porous formed article. Examples of the possible contaminating impurity element include nitrogen (nitrate nitrogen, nitrite nitrogen and ammonium nitrogen), sodium, magnesium, sulfur, chlorine, potassium, calcium, copper, zinc, bromine, barium and hafnium.

The phosphate adsorbing agent for blood processing of the present embodiment has a biocompatible polymer in the surface of the porous formed article contained therein.

Poly(methoxyethyl acrylate) (PMEA) is preferably used as the biocompatible polymer present in the surface of the porous formed article according to the present embodiment.

The biocompatible polymer according to the present embodiment will be described by taking poly(methoxyethyl acrylate) (PMEA) as an example.

The biocompatibility of PMEA is mentioned in detail in Masaru Tanaka, "Material Biocompatibilizing Surface of Artificial Organ", BIO INDUSTRY, Vol 20, No. 12, 59-70 2003.

In this literature, PMEA and acrylate polymers having a different side chain structure for comparison thereof were prepared and evaluated for various markers of platelets, white blood cells, complements, and coagulation systems when blood was circulated. The literature states that, as a result, "the PMEA surface less activated blood components than other polymers. The PMEA surface is excellent in blood compatibility because a significantly small number of human platelets adheres to the PMEA surface with small morphological change in adhering platelets".

Thus, it is considered that the good biocompatibility of PMEA is not only due to the presence of an ester group in the structure, but is largely influenced by the state of a water molecule adsorbed to the surface thereof.

In ATR-IR, a wave incident on a sample is reflected by slightly crawling into the sample. It is therefore known that the infrared absorption of a region corresponding to the depth of this crawling can be measured. Meanwhile, the present inventors have also found that this measurement region of ATR-IR is almost equal to the depth of a "superficial layer" corresponding to the surface of a porous formed article. Specifically, the present inventors have completed the present invention by conceiving that: biocompatibility in a region almost equal in depth to the ATR-IR measurement region governs the biocompatibility of a phosphate adsorbing agent for blood processing; and the presence of PMEA in this region can provide a phosphate adsorbing agent for blood processing having given biocompatibility.

The ATR-IR measurement region depends on the wavelength of infrared light in air, the angle of incidence, the refractive index of prism, the refractive index of a sample, etc. and is usually a region within 1 μm from the surface.

PMEA present in the surface of the porous formed article can be confirmed by the pyrolysis-gas chromatography-mass spectrometry of the porous formed article. The presence of PMEA is predicted if a peak is found around 1735 $cm^{-1}$ in an infrared absorption curve in attenuated total reflection-infrared (ATR-IR) spectroscopy for the surface of the porous formed article. However, the peak therearound may be derived from other substances. Accordingly, PMEA-derived 2-methoxyethanol can be confirmed by the pyrolysis-gas chromatography-mass spectrometry to confirm the presence of PMEA.

PMEA has distinct solubility in a solvent. For example, PMEA is not dissolved in a 100% ethanol solvent, whereas some region thereof is dissolved in a water/ethanol mixed solvent depending on a mixing ratio thereof. At the mixing ratio within the soluble region, the peak intensity of a PMEA-derived peak (around 1735 $cm^{-1}$) is greater as the amount of water is larger.

In the porous formed article containing PMEA in the surface thereof, water permeation performance is rarely changed because the pore size of the porous formed article surface is less changed. Thus, its product design is easy. In the present embodiment, the porous formed article has PMEA in the surface thereof. For example, in the case of coating the porous formed article with PMEA, it is considered that an ultrathin membrane of PMEA adheres to the surface of the porous formed article and coats the porous formed article substantially without filling the pores. Particularly, PMEA has a small molecular weight and a short molecular chain, which are preferred because the structure of its coating membrane is less likely to be thick and is less likely to change the structure of the porous formed article. Furthermore, PMEA is preferred because this polymer is highly compatible with other substances, can be uniformly applied to the surface of the porous formed article, and can improve biocompatibility.

In the present embodiment, the weight-average molecular weight of PMEA can be measured by, for example, gel permeation chromatography (GPC).

In the present embodiment, for example, a coating method which involves injecting a coating solution containing PMEA dissolved therein to, from above, a column packed with the porous formed article is preferably used as a method for allowing PMEA to be contained in the surface of the porous formed article.

The phosphate adsorbing agent for blood processing of the present embodiment is preferably used in phosphate adsorption in the hemodialysis of dialysis patients. Blood composition is divided into plasma components and blood cell components. The plasma components are constituted by 91% of water, 7% of proteins, lipid components and inorganic salts. Phosphate in blood is present as a phosphate ion in the plasma components. The blood cell components are constituted by 96% of red blood cells, 3% of white blood cells and 1% of platelets. The size of the red blood cells is 7 to 8 µm in diameter. The size of the white blood cells is 5 to 20 µm in diameter. The size of the platelets is 2 to 3 µm in diameter.

The phosphate adsorbing agent for blood processing of the present embodiment comprises the porous formed article having a large abundance of the inorganic ion adsorbent on the outer surface, because the porous formed article has a most frequent pore size of 0.08 to 0.70 µm measured with a mercury porosimeter. Therefore, the phosphate adsorbing agent for blood processing can reliably adsorb phosphate ions even in high-speed fluid flow and is also excellent in the property of penetrating, diffusing, and adsorbing phosphate ions into the inside of the porous formed article. Furthermore, the phosphate adsorbing agent for blood processing prevents blood flowing properties from being reduced due to, for example, clogging with blood cell components or the like.

Furthermore, in the present embodiment, such a porous formed article having a biocompatible polymer in the surface thereof can be used as a more preferred phosphate adsorbing agent for blood processing.

The phosphate adsorbing agent for blood processing of the present embodiment comprising the porous formed article comprising an organic polymer resin and an inorganic ion adsorbent and having a most frequent pore size of 0.08 to 0.70 µm measured with a mercury porosimeter, and having a biocompatible polymer in the surface of the porous formed article can selectively and reliably adsorb phosphate ions in blood. As a result, the phosphate concentration in blood brought back into the body is almost zero. The blood substantially free from phosphate is brought back into the body so that phosphate migrates actively from within or without cells into the blood, probably enhancing a refilling effect.

There is a possibility that a refilling effect to complement phosphate in blood can be induced to thereby excrete phosphate present within extracellular fluids and cells, which usually cannot be excreted.

In the phosphate adsorbing agent for blood processing of the present embodiment, a water-soluble polymer may be used as a component constituting the porous formed article.

Specifically, the porous formed article contained in the phosphate adsorbing agent for blood processing of the present embodiment may comprise an organic polymer resin, a water-soluble polymer and an inorganic ion adsorbent, have a most frequent pore size of 0.08 to 0.70 µm measured with a mercury porosimeter, and have a biocompatible polymer in the surface thereof.

In this case, the combination of the organic polymer resin, the water-soluble polymer and the inorganic ion adsorbent can be any combination of the respective components described in the present specification as the examples of the organic polymer resin, the water-soluble polymer and the inorganic ion adsorbent. Use of polyvinylpyrrolidone as the water-soluble polymer and PMEA as the biocompatible polymer can improve adsorption performance for phosphate in blood and biocompatibility at the same time. Although the mechanism thereof has not yet been elucidated, the improved compatibility between polyvinylpyrrolidone and PMEA present in the surface of the porous formed article presumably improves PMEA adsorption performance during PMEA coating to form more stable surface.

Accordingly, the phosphate adsorbing agent for blood processing can properly control phosphate concentrations in blood in the body without causing adverse reactions in dialysis patients even if the dialysis patients take no oral phosphate adsorbing agent or take only a small amount of an oral phosphate adsorbing agent (auxiliary use).

An appropriate column or the like packed with the phosphate adsorbing agent for blood processing of the present embodiment can be connected in series, in parallel or the like upstream or downstream of a dialyzer, and used in dialysis. A column or the like can be packed with the phosphate adsorbing agent for blood processing of the present embodiment and used as a column for phosphate adsorption. The resulting column for phosphate adsorption is excellent in selectivity and adsorption performance for inorganic phosphate even in a state where blood has a low phosphate concentration and the space velocity is fast.

The column packed with the phosphate adsorbing agent for blood processing of the present embodiment is preferably connected upstream or downstream of a dialyzer and used, from the viewpoint of easily inducing a refilling effect.

The phosphate adsorption rate (%) (rate at which phosphate in blood is adsorbed) is preferably 50% or more, more preferably 60% or more, further preferably 70% or more, 80% or more, 85% or more, 90% or more, 95% or more or 99% or more, from the viewpoint that a refilling effect can be expected.

In the phosphate adsorbing agent for blood processing of the present embodiment, the ratio of the amount of phosphate adsorbed to the phosphate adsorbing agent for blood processing to the amount of phosphate adsorbed to the porous formed article is preferably 1.01 or more.

The ratio of the amounts of phosphate adsorbed is not particularly limited and can be measured on the basis of the amounts of phosphate adsorbed measured in Examples. Preferably, the ratio can be determined from the amounts of phosphate adsorbed in water.

[Method for Producing Porous Formed Article]

A method for producing the porous formed article according to the present embodiment comprises the steps of: (1) crushing and mixing a good solvent for the organic polymer resin and the inorganic ion adsorbent to obtain slurry; (2) dissolving the organic polymer resin and a water-soluble polymer in the slurry obtained in the step (1); (3) shape-forming the slurry obtained in the step (2); (4) promoting coagulation of the shape-formed product obtained in the step (3) by controlling the temperature and humidity of a spatial portion coming into contact with the shape-formed product, until the shape-formed product is coagulated in a poor solvent; and (5) coagulating the coagulation-promoted shape-formed product obtained in the step (4), in a poor solvent.

(Step (1): Crushing and Mixing Step)

In the step (1), a good solvent for the organic polymer resin and the inorganic ion adsorbent are crushed and mixed to obtain slurry.

The inorganic ion adsorbent can be wet-crushed in the good solvent for the organic polymer resin to thereby finely pulverize the inorganic ion adsorbent. As a result, the inorganic ion adsorbent carried by the porous formed article after shape forming has only a small amount of secondary aggregates.

<Good Solvent for Organic Polymer Resin>

The good solvent for the organic polymer resin in the step (1) is not particularly limited as long as the good solvent stably dissolves more than 1% by mass of the organic polymer resin under production conditions for the porous formed article. A good solvent conventionally known in the art can be used.

Examples of the good solvent include dimethyl sulfoxide (DMSO), N-methyl-2-pyrrolidone (NMP), N,N-dimethylacetamide (DMAC) and N,N-dimethylformamide (DMF).

Only one of these good solvents may be used, or two or more thereof may be used as a mixture.

<Crushing and Mixing Unit>

In the step (1), the crushing and mixing unit used to obtain slurry is not particularly limited as long as the inorganic ion adsorbent and the good solvent for the organic polymer resin can be crushed and mixed together.

For example, a unit for use in a physical disruption method such as crushing under pressure, mechanical grinding or ultrasonic treatment can be used as the crushing and mixing unit.

Specific examples of the crushing and mixing unit include generator shaft-type homogenizers, blenders such as Waring blenders, media agitation mills such as sand mills, ball mills, attritors and beads mills, jet mills, mortars and pestles, stone mills and ultrasonic baths.

Among them, a media agitation mill is preferred because the media agitation mill has high crushing efficiency and can crush even highly viscous matter.

The ball size for use in the media agitation mill is not particularly limited and is preferably 0.1 to 10 mm. When the ball size is 0.1 mm or larger, the ball mass is sufficient. Therefore, the resulting media agitation mill has crushing power and high crushing efficiency. When the ball size is 10 mm or smaller, the resulting media agitation mill is excellent in finely crushing ability.

Examples of the material of the ball for use in the media agitation mill include, but are not particularly limited to, metals such as iron and stainless, oxides such as alumina and zirconia, and various ceramics of non-oxides such as silicon nitride and silicon carbide. Among them, zirconia is excellent in terms of excellent abrasion resistance and low contamination of products (contamination by abrasive matter).

<Dispersant>

In the step (1), a dispersant known in the art, such as a surfactant, may be added into the good solvent for the organic polymer resin mixed with the inorganic ion adsorbent during the crushing and mixing, without influencing the structure of the porous formed article.

(Step (2): Dissolution Step)

In the step (2), the organic polymer resin and a water-soluble polymer are dissolved in the slurry obtained by the step (1) to obtain slurry for shape forming.

The amount of the organic polymer resin added is preferably set such that an organic polymer resin/(organic polymer resin+water-soluble polymer+good solvent for the organic polymer resin) ratio is 3 to 40% by mass, more preferably 4 to 30% by mass. When the content of the organic polymer resin is 3% by mass or more, the resulting porous formed article has high strength. When the content is 40% by mass or less, the resulting porous formed article has a high porosity.

<Water-Soluble Polymer>

The water-soluble polymer in the step (2) is not particularly limited as long as the water-soluble polymer is compatible with the good solvent for the organic polymer resin and the organic polymer resin.

Any of natural, semisynthetic and synthetic polymers can be used as the water-soluble polymer.

Examples of the natural polymer include guar gum, locust bean gum, carrageenan, gum arabic, tragacanth, pectin, starch, dextrin, gelatin, casein and collagen.

Examples of the semisynthetic polymer include methylcellulose, ethylcellulose, hydroxyethylcellulose, ethylhydroxyethylcellulose, carboxymethyl starch and methyl starch.

Examples of the synthetic polymer include polyvinyl alcohol, polyvinylpyrrolidone, polyvinyl methyl ether, carboxyvinyl polymers, sodium polyacrylate and polyethylene glycols such as tetraethylene glycol and triethylene glycol.

Among them, a synthetic polymer is preferred from the viewpoint of enhancing carrying properties for the inorganic ion adsorbent, and polyvinylpyrrolidone and polyethylene glycols are more preferred from the viewpoint of improving porosity.

The mass-average molecular weights of the polyvinylpyrrolidone and the polyethylene glycols are preferably 400 to 35,000,000, more preferably 1,000 to 1,000,000, further preferably 2,000 to 100,000.

When the mass-average molecular weight is 2,000 or larger, the resulting porous formed article has high surface opening properties. When the mass-average molecular weight is 1,000,000 or smaller, shape forming tends to be easy because of the low viscosity of the slurry during the shape forming.

The mass-average molecular weight of the water-soluble polymer can be measured by the gel permeation chromatography (GPC) analysis of the water-soluble polymer dissolved in a predetermined solvent.

The amount of the water-soluble polymer added is preferably set such that a water-soluble polymer/(water-soluble polymer+organic polymer resin+good solvent for the organic polymer resin) ratio is 0.1 to 40% by mass, more preferably 0.5 to 30% by mass, further preferably 1 to 10% by mass.

When the amount of the water-soluble polymer added is 0.1% by mass or more, a porous formed article containing a fibrous structure where a three-dimensionally continuous network structure is formed in the outer surface and inside of the porous formed article is homogeneously obtained. When the amount of the water-soluble polymer added is 40% by mass or less, the outer surface opening ratio is proper. The resulting porous formed article can reliably adsorb ions even in high-speed fluid flow because the abundance of the inorganic ion adsorbent on the outer surface of the porous formed article is large.

(Step (3): Shape Forming Step)

In the step (3), the slurry (slurry for shape forming) obtained by the step (2) is shape-formed. The slurry for shape forming is mixed slurry of the organic polymer resin, the good solvent for the organic polymer resin, the inorganic ion adsorbent and the water-soluble polymer.

The form of the porous formed article according to the present embodiment can adopt any form of particles, a thread, a sheet, a hollow fiber, a cylinder, a hollow cylinder and the like, depending on a method for shape-forming the slurry for shape forming.

Examples of the method for shape-forming the slurry into the form of particles include, but are not particularly limited to, a rotary nozzle method which involves using a nozzle disposed on the side of a rotating container so that the slurry for shape forming contained in the container is scattered from the nozzle to form liquid drops. By the rotary nozzle method, the slurry can be shape-formed into the form of particles having a uniform particle size distribution.

The diameter of the nozzle is preferably 0.1 to 10 mm, more preferably 0.1 to 5 mm. The nozzle having a diameter of 0.1 mm or larger easily scatters liquid drops. The nozzle having a diameter of 10 mm or smaller can render the particle size distribution uniform.

The centrifugal force is indicated by centrifugal acceleration and is preferably 5 to 1500 G, more preferably 10 to 1000 G, further preferably 10 to 800 G.

When the centrifugal acceleration is 5 G or larger, the formation of liquid drops and scattering are easy. When the centrifugal acceleration is 1500 G or smaller, the slurry for shape forming is discharged without becoming the form of a thread, and can prevent the particle size distribution from being widened. The narrow particle size distribution has the advantage that a column packed with the porous formed article has uniform water flow channels and therefore prevents ions (object to be adsorbed) from leaking out (breaking through the column) from the initial stage of flushing even if ultrahigh-speed flushing is used.

Examples of the method for shape-forming the slurry into the form of a thread or a sheet include a method which involves extruding the slurry for shape forming from a spinneret or a die having the corresponding shape, and coagulating the extrudate in a poor solvent.

The method for shape-forming the slurry into a porous formed article in the form of a hollow fiber employs a spinneret consisting of a circular orifice and can thereby shape-form the slurry in the same way as the method for shape-forming the slurry into a porous formed article in the form of a thread or a sheet.

The method for shape-forming the slurry into a porous formed article in the form of a cylinder or a hollow cylinder may coagulate the extrudate of the slurry for shape forming from a spinneret in a poor solvent while cutting the extrudate or may coagulate the extrudate into the form of a thread and then cut the thread.

(Step (4): Coagulation Promotion Step)

In the step (4), coagulation of the shape-formed product obtained by the step (3) is promoted by controlling the temperature and humidity of a spatial portion coming into contact with the shape-formed product, until the shape-formed product is coagulated in a poor solvent.

The step (4) can adjust the most frequent pore size and the outer surface opening ratio measured with a mercury porosimeter, and produces a formed article having a high abundance of the inorganic ion adsorbent. The porous formed article provided thereby can remove ions, particularly, phosphate ions, in water to be processed at an ultrahigh speed and has a large adsorption capacity.

The temperature and humidity of the spatial portion are controlled by covering the space between a coagulation vessel in which the poor solvent is retained and the rotary container with a cover to adjust the temperature of the poor solvent.

The temperature of the spatial portion is preferably 20 to 90° C., more preferably 25 to 85° C., further preferably 30 to 80° C.

When the temperature of the spatial portion is 20° C. or higher, the outer surface opening ratio of the porous formed article is increased. When the temperature is 90° C. or lower, the nozzle opening in the rotary container is less likely to be clogged by the slurry. Thus, the porous formed article can be stably produced for a long time.

The humidity of the spatial portion is relative humidity at the temperature and is preferably 65 to 100%, more preferably 70 to 100%, further preferably 75 to 100%.

When the relative humidity is 65% or higher, the outer surface opening ratio of the porous formed article is increased. When the relative humidity is 100% or lower, the nozzle opening in the rotary container is less likely to be clogged by the slurry. Thus, the porous formed article can be stably produced for a long time.

(Step (5): Coagulation Step)

In the step (5), the coagulation-promoted shape-formed product obtained in the step (4) is coagulated in a poor solvent to obtain a porous formed article.

<Poor Solvent>

A solvent having an organic polymer resin solubility of 1% by mass or less under the conditions of the step (5) can be used as the poor solvent in the step (5). Examples thereof include water, alcohols such as methanol and ethanol, ethers and aliphatic hydrocarbons such as n-hexane and n-heptane. Among them, water is preferred as the poor solvent.

In the step (5), the good solvent is brought in from the preceding steps so that the concentration of the good solvent varies between the start of the coagulation step and the end thereof. Therefore, the poor solvent may be supplemented with the good solvent in advance. It is preferred to perform the coagulation step by controlling the concentration while separately adding water or the like so as to maintain the initial concentration.

The concentration of the good solvent can be adjusted to thereby control the structure (outer surface opening ratio and particle shape) of the porous formed article.

When the poor solvent is water or a mixture of the good solvent for the organic polymer resin and water, the content of the good solvent for the organic polymer resin with respect to water in the coagulation step is preferably 0 to 80% by mass, more preferably 0 to 60% by mass.

When the content of the good solvent for the organic polymer resin is 80% by mass or less, the effect of improving the shape of the porous formed article is obtained.

The temperature of the poor solvent is preferably 40 to 100° C., more preferably 50 to 100° C., further preferably 60 to 100° C., from the viewpoint of controlling the temperature and humidity of the spatial portion in the step (4).

(Production Apparatus for Porous Formed Article)

A production apparatus for the porous formed article according to the present embodiment has a rotary container which scatters liquid drops by centrifugal force, and a coagulation vessel which retains a coagulating liquid, and has a control unit which has a cover put over a spatial portion between the rotary container and the coagulation vessel and controls the temperature and humidity of the spatial portion.

The rotary container which scatters liquid drops by centrifugal force is not limited by a specific structure as long as the rotary container has the function of scattering the slurry for shape forming as spherical liquid drops by centrifugal force. Examples thereof include well-known rotary discs and rotary nozzles.

The rotary disc is configured such that the slurry for shape forming is supplied to the center of the rotating disc and then developed in a film form with a uniform thickness along the surface of the rotating disc so that the slurry is split dropwise by centrifugal force from the rim of the disc to scatter very small liquid drops.

The rotary nozzle is configured such that a large number of through-holes are formed in the peripheral wall of a hollow disc-shaped rotary container or a nozzle is attached to the rotary container so as to penetrate the peripheral wall, and the slurry for shape forming is supplied into the rotary container while the rotary container is rotated so that the slurry for shape forming is discharged by centrifugal force from the through-holes or the nozzle to form liquid drops.

The coagulation vessel which retains a coagulating liquid is not limited by a specific structure as long as the coagulation vessel has the function of being capable of retaining the coagulating liquid. Examples thereof include well-known coagulation vessels having an upper opening, and coagulation vessels having a structure where the coagulating liquid spontaneously flows downward by gravity along the inner face of a tubular body disposed so as to surround the rotary container.

The coagulation vessel having an upper opening is an apparatus in which the liquid drops scattered in a horizontal direction from the rotary container spontaneously flow downward and are then captured by the surface of the coagulating liquid retained in the coagulation vessel having an upper opening.

The coagulation vessel having a structure where the coagulating liquid spontaneously flows downward by gravity along the inner face of a tubular body disposed so as to surround the rotary container is an apparatus in which the coagulating liquid flows out in almost equal flow volumes in the circumferential direction along the inner face of the tubular body and spontaneously flows downward along the inner face so that the liquid drops are captured into the coagulating liquid flow and coagulated.

The control unit for the temperature and humidity of the spatial portion has a cover put over the spatial portion between the rotary container and the coagulation vessel and controls the temperature and humidity of the spatial portion.

The cover put over the spatial portion is not limited by a specific structure as long as the cover has the function of isolating the spatial portion from the external environment and facilitating practically controlling the temperature and humidity of the spatial portion. The cover can have, for example, a box, tubular, or umbrella shape.

Examples of the material of the cover include metallic stainless steels and plastics. The cover may be covered with a heat insulation material known in the art in terms of isolation from the external environment. The cover may be provided with a partial opening for temperature and humidity adjustment.

The control unit for the temperature and humidity of the spatial portion is not limited by a specific unit as long as the control unit has the function of controlling the temperature and humidity of the spatial portion. Examples thereof include heaters such as electric heaters and steam heaters and humidifiers such as ultrasonic humidifiers and heating humidifiers.

A unit of warming the coagulating liquid retained in the coagulation vessel and controlling the temperature and humidity of the spatial portion through the use of steam generated from the coagulating liquid is preferred in terms of a convenient structure.

The method for allowing PMEA to be contained in the surface of the porous formed article will be described in detail.

In the present embodiment, for example, a coating membrane can be formed by applying a coating solution containing PMEA to the surface of the porous formed article. In this respect, the coating solution may enter the pores formed in the porous formed article, and the porous formed article surface may be coated with PMEA with small change in pore size so that PMEA is contained throughout the pore surface of the porous formed article.

The coating solution is not particularly limited as long as the solvent does not dissolve the polymers, such as the organic polymer resin or the water-soluble polymer, constituting the porous formed article and can dissolve or disperse PMEA. Water or an aqueous alcohol solution is preferred because of process safety and good handling in a subsequent drying step. Water, an aqueous ethanol solution, an aqueous methanol solution, an aqueous isopropyl alcohol solution, or the like is preferably used from the viewpoint of a boiling point and toxicity.

The type and composition of the solvent in the coating solution are appropriately set in relation to the polymers constituting the porous formed article.

The concentration of PMEA in the coating solution is not limited and can be, for example, 0.001% by mass to 1% by mass, more preferably 0.005% by mass to 0.2% by mass, of the coating solution.

The method for applying the coating solution is not limited and can adopt, for example, a method which involves packing an appropriate column with the porous formed article, injecting the coating solution containing PMEA from above, and subsequently removing an extra solution using compressed air.

Then, the remaining unnecessary solvent is replaced and removed by washing with distilled water or the like. Then, the resultant can be sterilized and used as a medical tool.

The blood processing system of the present embodiment comprises the phosphate adsorbing agent for blood processing of the present embodiment. Preferably, the blood processing system further comprises a blood purifier.

Figure 6:
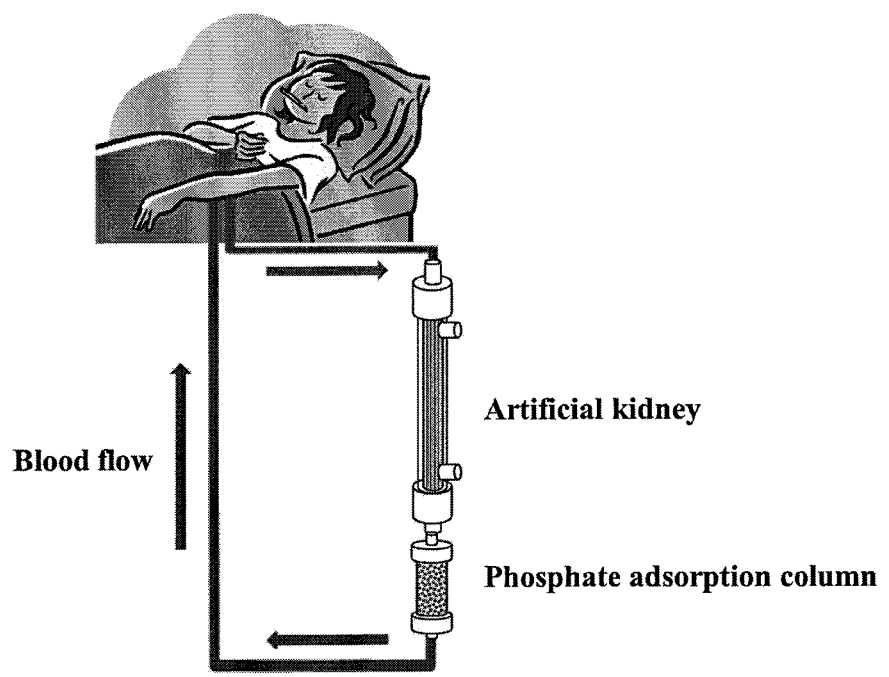
FIG. 6 is a schematic diagram showing the blood processing system according to the present embodiment.

It is preferred that the phosphate adsorbing agent for blood processing should be disposed such that blood processed by the blood purifier of the present embodiment is processed by the phosphate adsorbing agent for blood processing. FIG. 6 is a schematic diagram showing the blood processing system according to one embodiment.

Also, it is preferred that the phosphate adsorbing agent for blood processing should be disposed such that blood processed by the phosphate adsorbing agent for blood processing of the present embodiment is processed by the blood purifier.

The phosphate adsorbing agent for blood processing is preferably disposed in series or in parallel upstream or downstream of the blood purifier.

Examples of the blood purifier include, but are not particularly limited to, an artificial kidney (dialyzer) for use in dialysis therapy or the like.

Examples of the blood purifier of the present embodiment include blood purifiers using a separation membrane comprising a polysulfone polymer and a polyvinylpyrrolidone.

<Polysulfone Polymer>

In the present embodiment, the polysulfone polymer is a polymer containing a sulfone (—SO$_2$—) group in its structure.

Examples of the polysulfone polymer include polyphenylene sulfone, polysulfone, polyarylethersulfone, polyethersulfone and copolymers thereof.

Only one of these polysulfone polymers may be used, or two or more thereof may be used as a mixture.

Among them, a polysulfone polymer represented by the following formula (1) or (2) is preferred from the viewpoint of controlling fractionating properties:

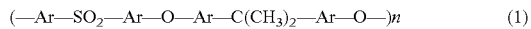

$$(-Ar-SO_2-Ar-O-Ar-C(CH_3)_2-Ar-O-)n \quad (1)$$

$$(-Ar-SO_2-Ar-O-)n \quad (2)$$

In the formulas (1) and (2), Ar represents a benzene ring, and n represents the repeat of the polymer and is an integer of 1 or larger.

Examples of the polysulfone polymer represented by the formula (1) include commercially available products under the name of "Udel (trademark)" from Solvay S.A. and under the name of "Ultrason (trademark)" from BASF Japan Ltd. Examples of the polyethersulfone represented by the formula (2) include commercially available products under the name of "Sumikaexcel (trademark)" from Sumitomo Chemical Co., Ltd. Some types exist depending on the degree of polymerization, etc. Therefore, these polymers can be appropriately used.

<Polyvinylpyrrolidone>

The polyvinylpyrrolidone is a water-soluble hydrophilic polymer prepared by vinyl-polymerizing N-vinylpyrrolidone, and is widely used as a material for hollow fiber membranes as a hydrophilizing agent or a hole forming agent.

For example, some polyvinylpyrrolidones differing in molecular weight are commercially available under the name of "Luvitec (trademark)" from BASF Japan Ltd. Therefore, these polymers can be appropriately used.

Only one of these polyvinylpyrrolidones may be used, or two or more thereof may be used as a mixture.

The separation membrane may comprise a constituent other than the polysulfone polymer and the polyvinylpyrrolidone as its constituents. Examples of the additional constituent include polyhydroxyalkyl methacrylates such as polyhydroxyethyl methacrylate, polyhydroxypropyl methacrylate and polyhydroxybutyl methacrylate and polyethylene glycol.

The content of the additional constituent in the separation membrane is not particularly limited. The content is 20% by mass or less and may be 10% by mass or less or may be 5% by mass or less.

In the separation membrane, the ratio of the polyvinylpyrrolidone to the polysulfone polymer is preferably 42% by mass or less because the amount of the polyvinylpyrrolidone eluted can be suppressed. The ratio of the polyvinylpyrrolidone to the polysulfone polymer is preferably 15% by mass or more, more preferably 20% by mass or more. When the ratio is 18% by mass or more, the polyvinylpyrrolidone concentration on the surface of the separation membrane can be controlled to within a preferred range. The resulting separation membrane for blood processing can be more effective for suppressing protein adsorption and be excellent in blood compatibility.

The shape of the separation membrane is not limited. The separation membrane preferably has a hollow fiber shape.

The separation membrane is preferably crimped from the viewpoint of permeation performance.

Hereinafter, a method for producing the blood purifier using a separation membrane comprising a polysulfone polymer and a polyvinylpyrrolidone will be described.

The separation membrane can be produced by membrane formation according to an ordinary method using a membrane forming dope containing at least the polysulfone polymer and the polyvinylpyrrolidone.

The membrane forming dope can be prepared by dissolving the polysulfone polymer and the polyvinylpyrrolidone in a solvent.

Examples of such a solvent include dimethylacetamide, dimethyl sulfoxide, N-methyl-2-pyrrolidone, dimethylformamide, sulfolane and dioxane.

Only one of these solvents may be used, or two or more thereof may be used as a mixture.

The concentration of the polysulfone polymer in the membrane forming dope is not particularly limited as long as the concentration falls within a range that permits membrane formation and allows the resulting separation membrane to have performance as a permeable membrane. The concentration is preferably 5 to 35% by mass, more preferably 10 to 30% by mass.

A lower polysulfone resin concentration is more preferred for achieving high water permeation performance. Thus, the concentration of the polysulfone polymer is further preferably 10 to 25% by mass.

The concentration of the polyvinylpyrrolidone in the membrane forming dope is not particularly limited. For example, the ratio of the polyvinylpyrrolidone to the polysulfone polymer (polyvinylpyrrolidone mass/polysulfone polymer mass) is preferably adjusted to 27% by mass or less, more preferably 18 to 27% by mass, further preferably 20 to 27% by mass.

When the ratio of the polyvinylpyrrolidone to the polysulfone polymer in the membrane forming dope is 27% by mass or less, the amount of the polyvinylpyrrolidone eluted can be suppressed. Preferably, when the ratio is 18% by mass or more, the polyvinylpyrrolidone concentration on the surface of the separation membrane can be controlled to within a preferred range. The resulting separation membrane can be more effective for suppressing protein adsorption and be excellent in blood compatibility.

The separation membrane can be formed as a flat membrane or a hollow fiber membrane by a method usually used using the membrane forming dope as mentioned above.

The method for producing the separation membrane will be described by taking a hollow fiber membrane as an example.

A tube-in-orifice spinneret is used. A membrane forming spinning dope and a bore liquid for coagulating the membrane forming spinning dope are discharged at the same time from the orifice and the tube, respectively, of the spinneret into the air. Water or a liquid composed mainly of water can be used as the bore liquid. In general, a mixed solution of the solvent used in the membrane forming spinning dope and water is preferably used. For example, an aqueous solution containing 20 to 70% by mass of dimethylacetamide is used.

The amount of the membrane forming spinning dope discharged and the amount of the bore liquid discharged can be adjusted to thereby adjust the inside diameter and membrane thickness of the hollow fiber membrane to the desired values.

The inside diameter of the hollow fiber membrane is not particularly limited and can be generally 170 to 250 μm, preferably 180 to 220 μm, for the purpose of blood processing. The membrane thickness of the hollow fiber membrane is preferably 50 μm or smaller from the viewpoint of the efficiency of diffusion and removal of low-molecular-weight matter by mass transfer resistance as a permeable membrane. The membrane thickness of the hollow fiber membrane is preferably 10 μm or larger from the viewpoint of strength.

The membrane forming spinning dope discharged together with the bore liquid from the spinneret is allowed to travel in an airgap portion, then introduced into a coagulation bath which is located beneath the spinneret and composed mainly of water, and dipped for a given time to complete the coagulation. In this respect, it is preferred that a draft indicated by the ratio between the linear speed of discharge of the membrane forming spinning dope and a take-up speed should be 1 or less.

The air gap means the space between the spinneret and the coagulation bath. The coagulation of the membrane forming spinning dope is started from the inner surface side by the poor solvent component (poor solvent component for the polysulfone polymer and the polyvinylpyrrolidone) such as water in the bore liquid discharged at the same time therewith from the spinneret. The draft is preferably 1 or less, more preferably 0.95 or less, for forming smooth separation membrane surface at the start of coagulation and stabilizing the separation membrane structure.

Subsequently, the solvent remaining in the hollow fiber membrane is removed by washing with hot water or the like. Then, the resultant can be introduced into a dryer in a continuous fashion and dried in hot air or the like to obtain a hollow fiber membrane. The washing is preferably carried out with hot water of 60° C. or higher for 120 seconds or longer, more preferably with hot water of 70° C. or higher for 150 seconds or longer, for removing unnecessary polyvinylpyrrolidone.

The water content of the separation membrane is preferably adjusted to 10% by mass or less by the drying, because the separation membrane is embedded in a urethane resin in a downstream process and sterilized by radiation in a dry state in the present embodiment.

The hollow fiber membrane obtained through these steps can be subjected, as a bundle with an adjusted length and number of fibers, to a module production step so as to attain the desired membrane area. In this step, the hollow fiber membrane is charged into a tubular container having two nozzles in the vicinity of both lateral ends, and embedded at its both ends with a urethane resin.

Then, the cured urethane moieties at both ends are cut off and thereby processed into end portions at which the hollow fiber membrane is opened (exposed). Header caps having a liquid inlet or outlet nozzle are respectively fitted in these end portions to fabricate the shape of a blood processor.

The blood processing method of the present embodiment comprises a phosphate adsorption step of processing blood using the phosphate adsorbing agent for blood processing of the present embodiment.

The blood processing method preferably comprises: a blood purification step of processing blood using a blood purifier; and the phosphate adsorption step before and/or after the blood purification step.

The phosphate adsorbing agent for blood processing is preferably used at the time of treatment with extracorporeal circulation and more preferably used at the time of hemodialysis treatment. The blood purifier for use in the treatment with extracorporeal circulation can remove phosphate in blood at a predetermined ratio by diffusion, filtration, adsorption and the like, and can therefore drastically improve the amount of blood processible by the phosphate adsorbing agent for blood processing by combined use with the phosphate adsorbing agent for blood processing. When the phosphate adsorbing agent for blood processing is disposed upstream of the blood purifier, the amount of phosphate removed based on elimination by the phosphate adsorption column is increased because of the high concentration of phosphate in blood entering the phosphate adsorption column. Also, there is a possibility that even if foreign matter is generated from the phosphate adsorbing agent due to some problem, an unsafe circumstance can be avoided by the blood purifier serving as a filter. Alternatively, when the blood purifier and the phosphate adsorbing agent for blood processing are disposed such that blood passes through the blood purifier and then the phosphate adsorbing agent and such that blood from which phosphate has already been removed at a given ratio is processed by the phosphate adsorbing agent for blood processing, there is a possibility that the amount of the phosphate adsorbing agent can be decreased by improving the amount of blood processible by the phosphate adsorbing agent for blood processing having a limited phosphate adsorption volume.

EXAMPLES

Hereinafter, in addition to Production Examples and Comparative Examples, the present invention will be described with reference to specific Examples and Comparative Control Examples. However, the present invention is not limited by these examples. The physical properties of the porous formed article were measured by the following methods.

[Observation of Porous Formed Article Under Scanning Electron Microscope]

The observation of the porous formed article under a scanning electron microscope (SEM) was performed using scanning electron microscope model SU-70 manufactured by Hitachi, Ltd.

The porous formed article sample was held on a carbon adhesive tape/alumina sample table and electro-conductively coated with osmium (Os) to prepare an outer surface SEM observation sample.

[Most Frequent Pore Size and Median Size Measured with Mercury Porosimeter]

The porous formed article was dried in vacuum at room temperature. Then, its most frequent pore size and median size were measured with a mercury porosimeter (manufactured by Shimadzu Corp., Shimadzu AutoPore model IV9500).

[Outer Surface Opening Ratio]

An image of the outer surface of the porous formed article photographed using a scanning electron microscope (SEM) was analyzed using image analysis software (manufactured by Asahi Kasei Engineering Corp., A-Zo-Kun (trade name)) to determine the outer surface opening ratio. More specifically, a threshold was manually adjusted such that the obtained SEM image was recognized as a grayscale image and the dark color portion and the light color portion corresponded to an opening and a porous structure (skeletal structure), respectively. The image was divided into the opening portion and the skeletal portion, and an area ratio thereof was determined. In order to reduce errors of threshold determination, the same measurement was performed for 10 images, and an average value was calculated.

[Specific Surface Area Measured with Mercury Porosimeter]

The porous formed article was dried in vacuum at room temperature. Then, the pore surface area S(Hg) ($m^2/g$) per unit mass of the porous formed article was measured using a mercury porosimeter (manufactured by Shimadzu Corp., Shimadzu AutoPore model IV9500).

Then, the porous formed article in a state wetted with water was tapped using a measuring cylinder, and its apparent volume V ($cm^3$) was measured. Then, the porous formed article was dried in vacuum at room temperature, and the dry mass W (g) of the porous formed article was determined.

The specific surface area of the porous formed article was determined according to the following expression:

Specific surface area ($m^2/cm^3$)=S(Hg)($m^2/g$)×Bulk specific gravity (g/$cm^3$)

Bulk specific gravity (g/$cm^3$)=$W/V$

In the expressions, S(Hg) is the surface area ($m^2/g$) per unit mass of the porous formed article, W is the dry mass (g) of the porous formed article, and V is the apparent volume ($cm^3$) thereof.

[Average Particle Size of Porous Formed Article and Average Particle Size of Inorganic Ion Adsorbent]

The average particle size of the porous formed article and the average particle size of the inorganic ion adsorbent were measured using a laser diffraction/scattering particle size distribution measurement apparatus (LA-950 (trade name) manufactured by HORIBA, Ltd.). Water was used as a dispersion medium. In the case of using hydrous cerium oxide as the inorganic ion adsorbent, the sample was assayed by using the value of cerium oxide as a refractive index. Likewise, in the case of using hydrous zirconium oxide as the inorganic ion adsorbent, the sample was assayed by using the value of zirconium oxide as a refractive index.

[ATR (Attenuated Total Reflection)-Infrared Spectroscopy]

Nicolet iN-10 manufactured by Thermo Fisher Scientific Inc. was used as an infrared analysis apparatus, and a germanium prism was used in ATR analysis.

Sample measurement was performed by the following procedures.

ATR-infrared spectroscopy was conducted (650 $cm^{-1}$ to 4000 $cm^{-1}$) with a germanium prism pressed against the outer surface portion of a porous formed article.

As a result of measuring a PMEA-coated sample and an uncoated sample, an infrared absorption peak of an ester group —O—C=O derived from PMEA around 1735 $cm^{-1}$ is seen in the PMEA-coated sample, whereas this peak is not seen in the uncoated sample. Therefore, the presence of PMEA in the surface of the porous formed article can be confirmed.

[Amount of Phosphate Adsorbed from Bovine Plasma]

The amount of phosphate adsorbed was measured by a column flow test using a low-phosphate concentration serum from bovine plasma. Although the details are described in Production Example 1 and Example 1, the amount of phosphate adsorbed (mg-P/mL-Resin (porous formed article)) of the porous formed article (phosphate adsorbing agent) packed in the column was measured under conditions equivalent to general dialysis conditions (space velocity SV=120, 4-hour dialysis) using bovine plasma adjusted to a low phosphate concentration (0.7 mg/dL).

The phosphate ion concentration was measured by the direct molybdate method.

A sample having an amount of phosphate adsorbed of 1.5 (mg-P/mL-Resin) or larger at a fluid flow rate of SV120 was assessed as being a good phosphate adsorbing agent having a large adsorption capacity.

Production Example 1

220 g of N-methyl-2-pyrrolidone (NMP, Mitsubishi Chemical Corp.) and 200 g of a hydrous cerium oxide powder having an average particle size of 30 µm (Iwatani Corp.) were added to a stainless ball mill pot (capacity: 1 L) packed with 1.5 kg of stainless balls having a diameter of 5 mmϕ, and subjected to crushing and mixing treatment at 75 rpm for 150 minutes to obtain yellow slurry. To the obtained slurry, 4 g of polyvinylpyrrolidone (PVP, BASF Japan Ltd., Luvitec K30 Powder (trade name)) and 10 g of a copolymer consisting of 91.5% by mass of acrylonitrile, 8.0% by mass of methyl acrylate and 0.5% by mass of sodium methallylsulfonate and having limiting viscosity [η]=1.2 (organic polymer resin, PAN) were added, and the mixture was warmed to 60° C. in a dissolution vessel and dissolved with agitation using an agitation blade to obtain a homogeneous slurry solution for shape forming.

The obtained slurry solution for shape forming was warmed to 60° C. and supplied to the inside of a cylindrical rotary container in which a nozzle having a diameter of 4 mm was opened on the lateral side. This container was rotated to form liquid drops from the nozzle by centrifugal force (15 G). Subsequently, the spatial portion between the rotary container and a coagulation vessel was covered with a polypropylene cover to control the temperature and relative humidity of the spatial portion to 50° C. and 100%, respectively. The liquid drops were allowed to travel in this spatial portion and arrive at a coagulating liquid (content of NMP with respect to water: 50% by mass) warmed to 80° C., which was retained in a coagulation vessel having an upper opening, to coagulate the slurry for shape forming.

Washing and classification were further performed to obtain a spherical porous formed article.

An electron microscope photograph (magnification: ×10,000) showing the surface of the obtained porous formed article is shown in FIG. 1.

(Measurement of Amount of Phosphate Adsorbed in Plasma in Batch Manner)

Blood was collected from healthy human donors. To 100 mL of the blood, 14 mL of a CPD solution (anticoagulant solution) was added, and the mixture was centrifuged to separate between blood cell components and plasma components.

The phosphate concentration (measurement method: direct molybdate method) in the plasma components was 11.1 mg/dL. Into 10 mL of the plasma, 0.1 mL of the porous formed article (washed in a saline solution) was added, and mixed therewith at room temperature for 2 hours. Then, the phosphate concentration in the plasma was measured. The amount of phosphate adsorbed to the porous formed article was calculated to be 8.7 mg-P/mL-Resin. Likewise, the amount of phosphate adsorbed to the porous formed article mixed at room temperature for 2 hours in an aqueous system (phosphate concentration: 12 mg/dL) was 11.2 mg-P/mL-Resin.

The obtained porous formed article had high phosphate selectivity and a large amount of phosphate adsorbed even in plasma, though the amount of phosphate adsorbed in the plasma was slightly lower as compared with the aqueous system.

(Blood Flow Test)

Figure 5:
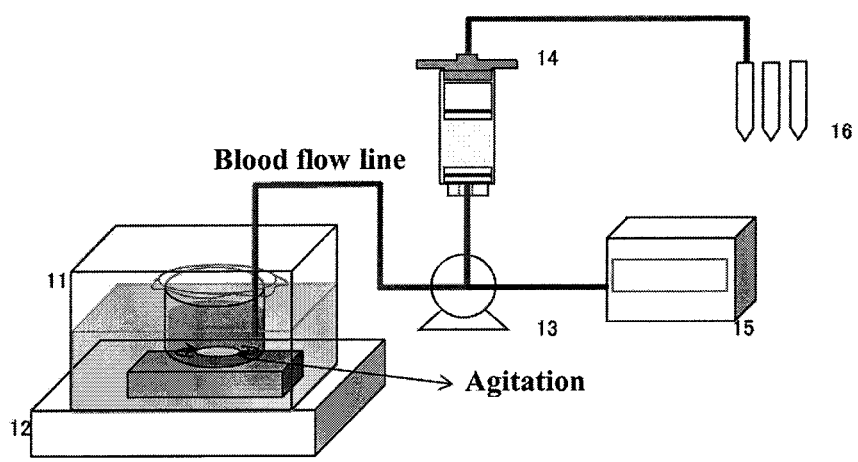
FIG. 5 is a schematic diagram showing a blood flow test in Production Example 1.

Change in pressure drop, hemolysis, blood cell adhesion (white blood cells WBC, red blood cells RBC and platelets PLT) and protein adsorbing properties were evaluated by the blood flow test according to the schematic diagram shown in FIG. 5.

To approximately 51 mL of healthy human blood, 1000 IU/L of an anticoagulant heparin was added to prepare a blood stock. The porous formed article and beads-shaped active carbon in Hemosorba CHS-350 (adsorption-type blood purifier manufactured by Asahi Kasei Medical Co., Ltd.) were selected as test samples.

Columns were each packed with a resin in an amount of 0.875 mL and washed with saline. Then, the blood stock was sent at a flow rate of 0.25 mL/min to the lower part of each column using a pump. A sample solution coming out of the upper part was fractionated at 3 mL/min.

1. Results about Change in Pressure Drop

Although the blood flow test was conducted for a flow time of approximately 200 minutes, no change in pressure drop was observed in both the samples. Clogging or the like did not occur. The pressure stayed at 1 kPa or lower.

2. Results about Hemolysis

Each sample was mixed with saline, and the mixture was left standing for 30 minutes or longer and then centrifuged, followed by the measurement of the absorbance Abs540 of the supernatant. Absorbance Abs540 from the blood stock and saline processed in the same way as above was defined as 0% degree of hemolysis, and absorbance Abs540 from the blood stock and distilled water processed in the same way as above was defined as 100% degree of hemolysis. The degree of hemolysis of each fraction was calculated.

The blood flow test was conducted for a flow time of approximately 200 minutes, and a sample solution was fractionated at 3 mL/min. The degree of hemolysis of each sample was measured. As a result, all of the samples had 0.5% or less degree of hemolysis, and no hemolysis was observed. This demonstrated that the porous formed article was actually used without any problem.

3. Results about Blood Cell Adhesion (White Blood Cells WBC, Red Blood Cells RBC, Platelets PLT)

The blood flow test was conducted for a flow time of approximately 200 minutes, and a sample solution was fractionated at 3 mL/min and analyzed.

A multi-item automatic blood cell analysis apparatus XT-1800i manufactured by Sysmex Corp. was used in the analysis.

None of the white blood cells, the red blood cells and the platelets differed in the adhesion rate between the porous formed article and Hemosorba CHS-350, demonstrating that the porous formed article was actually used without any problem.

4. Results about Protein Adsorbing Properties

The blood flow test was conducted for a flow time of approximately 200 minutes, and a sample solution was fractionated at 3 mL/min and analyzed.

The biuret method was used in the analysis. The absorbance of standard serum and the samples was measured at a wavelength of 540 nm to measure the amount of proteins adsorbed from the stock.

The amount of proteins adsorbed from the first fraction was 8 mg-P/mL-Resin for the porous formed article and 45 mg/mL-Hemosorba CHS-350 for Hemosorba CHS-350. Thus, the amount of proteins adsorbed on the porous formed article was smaller. The adsorption rates from the fractions subsequent to the first one were as small as 0 to 2 mg/mL for both the samples. This demonstrated that the porous formed article was actually used without any problem.

(Column Flow Test Using Low-Phosphate Concentration Serum from Bovine Plasma)

The inorganic phosphate concentration in blood at the outlet of a dialyzer at the time of dialysis treatment was 0.2 to 1.0 mg/dL. Therefore, the amount of phosphate adsorbed in this concentration range must be measured. Therefore, the phosphate concentration of a test plasma fluid was adjusted.

Commercially available bovine serum was centrifuged (3500 rpm, 5 min) to prepare 2000 mL of a supernatant plasma. The phosphate concentration in the plasma was 10.8 mg/dL.

To half (1000 mL) the amount of the obtained plasma, the porous formed article obtained in Production Example 1 was added, and the mixture was agitated at room temperature for 2 hours and centrifuged (3500 rpm, 5 min) to obtain approximately 950 mL of plasma having a phosphate concentration of 0.

33 mL of the plasma having a phosphate concentration of 10.8 mg/dL and 467 mL of the plasma having a phosphate concentration of 0 were mixed and centrifuged (3500 rpm, 5 min) to obtain 495 mL of plasma having a phosphate concentration of 0.7 mg/dL as a supernatant.

A column packed with 1 mL of the porous formed article was assembled according to the schematic diagram shown in FIG. 5. 450 mL of the obtained plasma was injected thereto at a flow rate of 2 mL/min. 10 mL was collected for the first fraction, and 20 mL/sample was collected for subsequent fractions. Average dialysis conditions typically involve performing dialysis at flow rate Qb=200 mL/min for 4 hours. Therefore, 200 mL×4 hours=48000 mL is obtained as a total blood flow volume. When blood cell components have Ht=30%, the flow volume of plasma is 33600 mL. Since this experiment was conducted on a scale of 1/100, fluid flow of 340 mL was used as a guideline.

Figure 7:
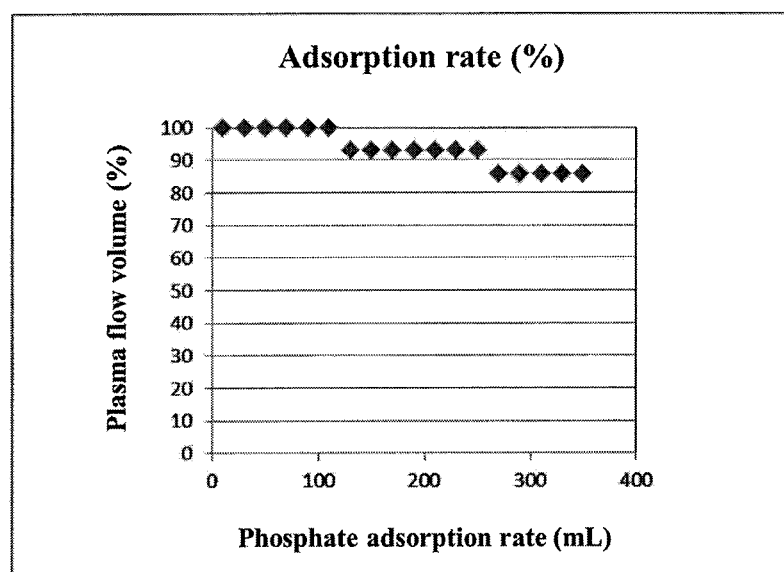
FIG. 7 shows the relationship between a plasma flow volume and a phosphate adsorption rate (%) in Production Example 1.

Table 1 shows the plasma flow volume, the column-outlet phosphate concentration, the phosphate adsorption rate (%) and the total amount adsorbed. Also, FIG. 7 shows the relationship between the plasma flow volume and the phosphate adsorption rate (%).

TABLE 1

| Fraction No. | Plasma flow volume (mL) | Outlet plasma concentration (mg/dL) | Phosphate adsorption rate (%) | Total amount adsorbed (mg-P/mL-Resin) |
|---|---|---|---|---|
| 1 | 10 | 0 | 100 | 0.07 |
| 2 | 30 | 0 | 100 | 0.21 |
| 3 | 50 | 0 | 100 | 0.35 |
| 4 | 70 | 0 | 100 | 0.49 |
| 5 | 90 | 0 | 100 | 0.63 |
| 6 | 110 | 0 | 100 | 0.77 |
| 7 | 130 | 0.05 | 93 | 0.90 |
| 8 | 150 | 0.05 | 93 | 1.03 |
| 9 | 170 | 0.05 | 93 | 1.16 |
| 10 | 190 | 0.05 | 93 | 1.29 |
| 11 | 210 | 0.05 | 93 | 1.42 |
| 12 | 230 | 0.05 | 93 | 1.55 |
| 13 | 250 | 0.05 | 93 | 1.68 |
| 14 | 270 | 0.1 | 86 | 1.80 |
| 15 | 290 | 0.1 | 86 | 1.92 |
| 16 | 310 | 0.1 | 86 | 2.04 |
| 17 | 330 | 0.1 | 86 | 2.16 |
| 18 | 350 | 0.1 | 86 | 2.28 |

The amount of phosphate adsorbed to the porous formed article at a plasma flow volume of 350 mL was 2.28 mg-P/mL-Resin.

The phosphate adsorption rate was 100% up to a plasma flow volume of 110 mL, and the adsorption rate was 86% even at the completion of dialysis. Therefore, a refilling effect can be expected.

The amount of phosphate eliminated by dialysis alone can be measured by analyzing the amount of a dialysis fluid. For example, data shows that the amount of phosphate eliminated by 4-hour dialysis can be 1100 mg. From a phosphate concentration in blood processed by a dialyzer in this dialysis, the amount of phosphate eliminable by a phosphate adsorbing member disposed downstream of the dialyzer can be calculated. For example, it can be estimated that 240 mg of phosphate is eliminable. This value is as large as 20% or more of the amount of phosphate eliminated by dialysis. However, this estimated value does not take a refilling effect on phosphate in the body into consideration. If the refilling effect can be expected, the amount of phosphate eliminated by dialysis may be increased while the amount of phosphate eliminated by the phosphate adsorbing member may also be increased. Thus, the total amount of phosphate eliminated may be considerably increased.

Production Example 2

A spherical porous formed article was obtained in the same way as the method described in Production Example 1 except that: the temperature of the coagulating liquid was set to 60° C.; and the temperature and relative humidity of the spatial portion were controlled to 37° C. and 100%, respectively.

Production Example 3

A spherical porous formed article was obtained in the same way as the method described in Production Example 1 except that the amount of the hydrous cerium oxide powder added was increased from 200 g to 300 g.

Production Example 4

A spherical porous formed article was obtained in the same way as the method described in Production Example 1 except that the amount of the hydrous cerium oxide powder added was decreased from 200 g to 150 g.

Production Example 5

A spherical porous formed article was obtained in the same way as the method described in Production Example 3 except that the nozzle on the lateral side of the cylindrical rotary container had a narrower diameter of 3 mm changed from 4 mm and was used in shape forming into the porous formed article.

Production Example 6

A spherical porous formed article was obtained in the same way as the method described in Production Example 3 except that the nozzle on the lateral side of the cylindrical rotary container had a thicker diameter of 5 mm changed from 4 mm and was used in shape forming into the porous formed article.

Production Example 7

A spherical porous formed article was obtained in the same way as the method described in Production Example 1 except that: the good solvent for the organic polymer resin was changed to 160 g of dimethyl sulfoxide (DMSO, Kanto Chemical Co., Inc.); the organic polymer resin was changed to 20 g of an ethylene vinyl alcohol copolymer (EVOH, The Nippon Synthetic Chemical Industry Co., Ltd., Soarnol E3803 (trade name)); the amount of the hydrous cerium oxide powder added was set to 250 g; the coagulating liquid was water; and the nozzle diameter was 5 mm.

Production Example 8

A spherical porous formed article was obtained in the same way as the method described in Production Example 1 except that: the organic polymer resin was changed to 30 g of polyethersulfone (Sumitomo Chemical Co., Ltd., Sumikaexcel 5003PS (trade name), OH-terminated grade, terminal hydroxy group composition: 90 (% by mol)); the water-soluble polymer was changed to 4 g of polyethylene glycol (PEG35,000, Merck Japan); the amount of the hydrous cerium oxide powder was set to 100 g; the coagulating liquid was water; and the nozzle diameter was 5 mm.

Production Example 9

A spherical porous formed article was obtained in the same way as the method described in Production Example 1 except that the inorganic ion adsorbent used was a hydrous zirconium oxide powder (Daiichi Kigenso Kagaku Kogyo Co., Ltd., R Zirconium Hydroxide (trade name)) dried with a constant mass in a dryer of 70° C.

Production Example 10

A spherical porous formed article was obtained in the same way as the method described in Production Example 7 except that: the inorganic ion adsorbent used was a hydrous zirconium oxide powder (Daiichi Kigenso Kagaku Kogyo Co., Ltd., R Zirconium Hydroxide (trade name)) dried with a constant mass in a dryer of 70° C.; and the nozzle diameter was 4 mm.

Production Example 11

A spherical porous formed article was obtained in the same way as the method described in Production Example 8 except that: the inorganic ion adsorbent used was a hydrous zirconium oxide powder (Daiichi Kigenso Kagaku Kogyo Co., Ltd., R Zirconium Hydroxide (trade name)) dried with a constant mass in a dryer of 70° C.; and the nozzle diameter was 4 mm.

Production Example 12

A spherical porous formed article was obtained in the same way as the method described in Production Example 1 except that: the temperature of the coagulating liquid was set to 50° C.; and the temperature and relative humidity of the spatial portion were controlled to 31° C. and 80%, respectively.

Production Example 13

154 g of N-methyl-2-pyrrolidone (NMP, Mitsubishi Chemical Corp.) and 300 g of a hydrous cerium oxide powder having an average particle size of 30 μm (Iwatani Corp.) were added to a stainless ball mill pot (capacity: 1 L) packed with 1.5 kg of stainless balls having a diameter of 5 mmϕ, and subjected to crushing and mixing treatment at 75 rpm for 150 minutes to obtain yellow slurry. To the obtained slurry, 15 g of polyethersulfone (Sumitomo Chemical Co., Ltd., Sumikaexcel 5003PS (trade name), OH-terminated grade) was added, and the mixture was warmed to 60° C. in a dissolution vessel and dissolved with agitation using an agitation blade to obtain a homogeneous slurry solution for shape forming.

The obtained slurry solution for shape forming was warmed to 60° C. and supplied to the inside of a cylindrical rotary container in which a nozzle having a diameter of 4 mm was opened on the lateral side. This container was rotated to form liquid drops from the nozzle by centrifugal force (15 G). The spatial portion between the rotary container and a coagulation vessel was covered with a polypropylene cover to control the temperature and relative humidity of the spatial portion to 30° C. and 70%, respectively. The liquid drops were allowed to travel in this spatial portion and arrive at a coagulating liquid (content of NMP with respect to water: 10% by mass) warmed to 40° C., which was retained in a coagulation vessel having an upper opening, to coagulate the slurry for shape forming.

Washing and classification were further performed to obtain a spherical porous formed article.

Production Example 14

A spherical porous formed article was obtained in the same way as the method described in Production Example 1 except that: 160 g of N-methyl-2-pyrrolidone (NMP, Mitsubishi Chemical Corp.) was used; the organic polymer resin was changed to 30 g of polyethersulfone (Sumitomo Chemical Co., Ltd., Sumikaexcel 5003PS (trade name), OH-terminated grade); the water-soluble polymer was changed to 4 g of polyethylene glycol (PEG35,000, Merck Japan); and the amount of the hydrous cerium oxide powder added was set to 100 g.

Production Example 15

A spherical porous formed article was obtained in the same way as the method described in Production Example 14 except that: the temperature of the coagulating liquid was set to 60° C.; and the temperature and relative humidity of the spatial portion were controlled to 37° C. and 90%, respectively.

Comparative Example 1

A porous formed article was obtained in the same way as the method described in Production Example 2 except that the spatial portion between the rotary container and the coagulation vessel was not covered with a polypropylene cover. The temperature and relative humidity of this spatial portion were 26° C. and 63%, respectively.

Comparative Example 2

A porous formed article was obtained with reference to Example 1 of International Publication No. WO 2011/062277.

A spherical porous formed article was obtained in the same way as the method described in Production Example 8 except that: the spatial portion between the rotary container and the coagulation vessel was not covered with a polypropylene cover; and the temperature of the coagulating liquid was set to 60° C. The temperature and relative humidity of this spatial portion were 26° C. and 63%, respectively.

Comparative Example 3

A porous formed article was obtained with reference to Example 2 of International Publication No. WO 2005/056175.

A spherical porous formed article was obtained in the same way as the method described in Production Example 7 except that: the spatial portion between the rotary container and the coagulation vessel was not covered with a polypropylene cover; and the temperature of the coagulating liquid was set to 60° C. The temperature and relative humidity of this spatial portion were 26° C. and 63%, respectively.

Tables 2 and 3 show the physical properties of the porous formed articles obtained in Production Examples 1 to 12 and Comparative Examples 1 to 3 and their total amounts adsorbed (mg-P/mL-Resin) when the plasma flow volume reached 350 mL under the same conditions as in Production Example 1.

TABLE 2

| Physical properties | Production Example 1 | Production Example 2 | Production Example 3 | Production Example 4 | Production Example 5 | Production Example 6 | Production Example 7 | Production Example 8 | Production Example 9 |
| --- | --- | --- | --- | --- | --- | --- | --- | --- | --- |
| Organic polymer resin | PAN | PAN | PAN | PAN | PAN | PAN | EVOH | PES | PAN |
| Inorganic ion adsorbent | C | C | C | C | C | C | C | C | Z |
| Presence or absence of cover used for spatial portion | Present | Present | Present | Present | Present | Present | Present | Present | Present |
| Relative humidity of spatial portion (%) | 100 | 100 | 100 | 100 | 100 | 100 | 100 | 100 | 100 |
| Temperature of spatial portion (° C.) | 50 | 37 | 50 | 50 | 50 | 50 | 50 | 50 | 50 |
| Coagulating liquid temperature (° C.) | 80 | 60 | 80 | 80 | 80 | 80 | 80 | 80 | 80 |
| Coagulating liquid composition (good solvent/water) | 50/50 | 50/50 | 50/50 | 50/50 | 50/50 | 50/50 | 0/100 | 0/100 | 50/50 |
| Average particle size (μm) | 370 | 370 | 370 | 370 | 300 | 550 | 530 | 600 | 370 |
| Outer surface opening ratio (%) | 20 | 10 | 20 | 20 | 21 | 20 | 27 | 19 | 21 |
| Presence or absence of skin layer | Absent | Absent | Absent | Absent | Absent | Absent | Absent | Absent | Absent |
| most frequent | pore size measured with porosimeter (μm) | 0.41 | 0.40 | 0.37 | 0.27 | 0.35 | 0.36 | 0.40 | 0.34 | 0.40 |
| Median size measured with porosimeter (μm) | 0.40 | 0.37 | 0.31 | 0.28 | 0.32 | 0.31 | 0.36 | 0.31 | 0.41 |
| most frequent | pore size/median size ratio | 1.03 | 1.08 | 1.19 | 0.96 | 1.09 | 1.16 | 1.11 | 1.10 | 0.98 |

TABLE 2-continued

| Physical properties | Production Example 1 | Production Example 2 | Production Example 3 | Production Example 4 | Production Example 5 | Production Example 6 | Production Example 7 | Production Example 8 | Production Example 9 |
|---|---|---|---|---|---|---|---|---|---|
| Specific surface area measured with porosimeter ($m^2/cm^3$) | 18 | 18 | 22 | 14 | 22 | 22 | 20 | 12 | 17 |
| Bulk specific gravity ($g/cm^3$) | 0.52 | 0.52 | 0.64 | 0.45 | 0.65 | 0.64 | 0.62 | 0.36 | 0.51 |
| Amount of phosphate adsorbed (mg-P/mL-Resin) in plasma Condition of SV120, 350 ml of plasma processed | 2.28 | 2.11 | 2.55 | 1.81 | 3.05 | 1.65 | 1.64 | 1.61 | 1.89 |

C: hydrous cerium oxide
Z: zirconium hydroxide

TABLE 3

| Physical properties | Production Example 10 | Production Example 11 | Production Example 12 | Production Example 13 | Production Example 14 | Production Example 15 | Comparative Example 1 | Comparative Example 2 | Comparative Example 3 |
|---|---|---|---|---|---|---|---|---|---|
| Organic polymer resin | EVOH | PES | PAN | PES | PES | PES | PAN | PES | EVOH |
| Inorganic ion adsorbent | Z | Z | C | C | C | C | C | C | C |
| Presence or absence of cover used for spatial portion | Present | Present | Present | Present | Present | Present | Absent | Absent | Absent |
| Relative humidity of spatial portion (%) | 100 | 100 | 80 | 70 | 100 | 90 | 63 | 63 | 63 |
| Temperature of spatial portion (° C.) | 50 | 50 | 31 | 30 | 50 | 37 | 26 | 26 | 26 |
| Coagulating liquid temperature (° C.) | 80 | 80 | 50 | 40 | 80 | 80 | 60 | 60 | 60 |
| Coagulating liquid composition (good solvent/water) | 0/100 | 0/100 | 50/50 | 10/90 | 50/50 | 50/50 | 50/50 | 0/100 | 0/100 |
| Average particle size (μm) | 370 | 370 | 370 | 370 | 370 | 370 | 370 | 600 | 530 |
| Outer surface opening ratio (%) | 20 | 18 | 6 | 5 | 29 | 15 | 4 | 3 | 30 |
| Presence or absence of skin layer | Absent | Absent | Absent | Absent | Absent | Absent | Absent | Absent | Absent |
| most frequent pore size measured with porosimeter (μm) | 0.39 | 0.35 | 0.39 | 0.08 | 0.67 | 0.55 | 0.78 | 0.07 | 2.00 |
| Median size measured with porosimeter (μm) | 0.41 | 0.31 | 0.36 | 0.07 | 0.53 | 0.51 | 0.59 | 0.09 | 1.65 |
| most frequent pore size/median size ratio | 0.95 | 1.13 | 1.08 | 1.14 | 1.26 | 1.08 | 1.32 | 0.78 | 1.21 |
| Specific surface area measured with porosimeter ($m^2/cm^3$) | 16 | 17 | 17 | 29 | 15 | 16 | 17 | 8 | 4 |
| Bulk specific gravity ($g/cm^3$) | 0.51 | 0.51 | 0.52 | 0.87 | 0.45 | 0.45 | 0.51 | 0.36 | 0.61 |
| Amount of phosphate adsorbed (mg-P/mL-Resin) in plasma Condition of SV120, 350 ml of plasma processed | 1.77 | 1.68 | 1.92 | 1.66 | 1.91 | 2.67 | 0.43 | 0.52 | 1.09 |

C: hydrous cerium oxide
Z: zirconium hydroxide

Production Example 16 and Comparative Example 4

(Preparation of Blood Processor)

A membrane forming spinning dope was prepared by dissolving 17 parts by mass of polysulfone (manufactured by Solvay S.A., P-1700) and 4 parts by mass of polyvinylpyrrolidone (manufactured by BASF Japan Ltd., K-90) in 79 parts by mass of dimethylacetamide (manufactured by Kishida Chemical Co., Ltd., special grade reagent).

An aqueous solution containing 60% by mass of dimethylacetamide was used as a bore liquid.

The membrane forming spinning dope and the bore liquid were discharged from a tube-in-orifice spinneret. The temperature of the membrane forming spinning dope at the time of discharge was set to 40° C. The discharged membrane forming spinning dope was passed through a hooded fall portion, dipped in a coagulation bath of 60° C. consisting of water, and coagulated. The spinning speed was set to 30 m/min.

After the coagulation, the resultant was washed with water and dried to obtain a hollow fiber separation membrane. The water washing temperature was set to 90° C., and the water washing time was set to 180 seconds. The amounts of the membrane forming spinning dope and the bore liquid discharged were adjusted such that the membrane thickness and the inside diameter after drying were 45 μm and 185 μm, respectively.

The obtained hollow fiber separation membrane was incorporated in a blood processing container and shape-formed, and a module having an effective area of 0.02 $m^2$ was fabricated to obtain a blood processor.

Figure 8:
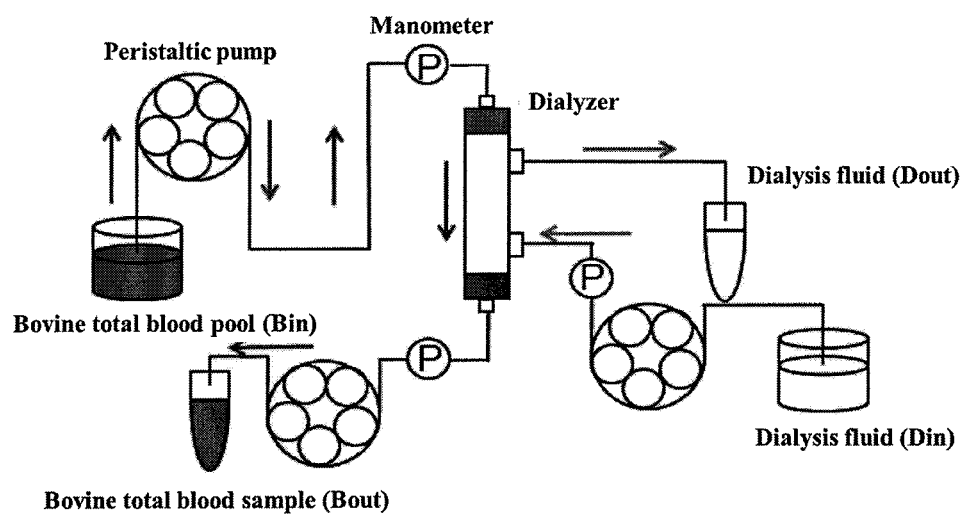
FIG. 8 is a schematic diagram showing circuit 1 for the measurement test of the amount of phosphate removed in Production Example 16 and Comparative Example 4.

The amount of phosphate removed was measured in circuit 1 (FIG. 8) using the obtained blood processor.

Figure 9:
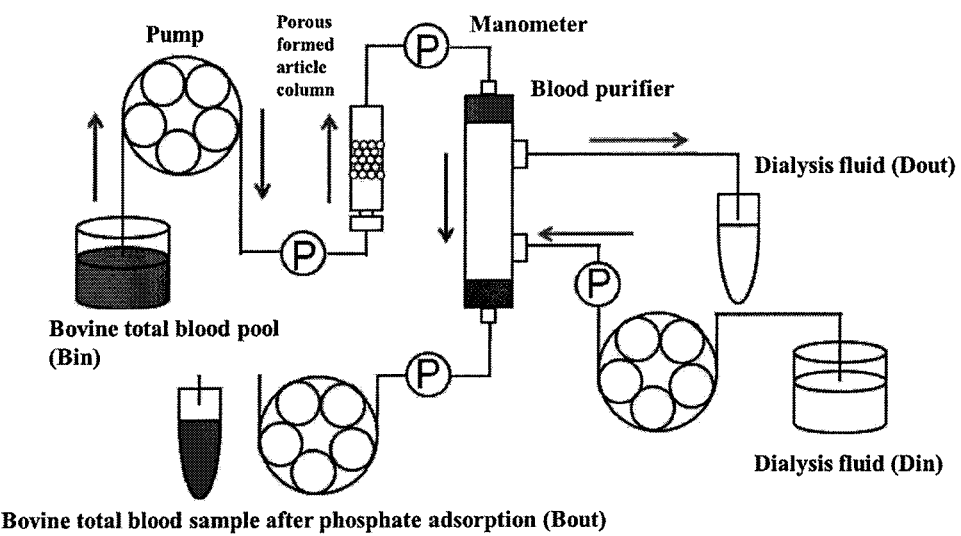
FIG. 9 is a schematic diagram showing circuit 2 for the measurement test of the amount of phosphate removed in Production Example 16 and Comparative Example 4.
Figure 10:
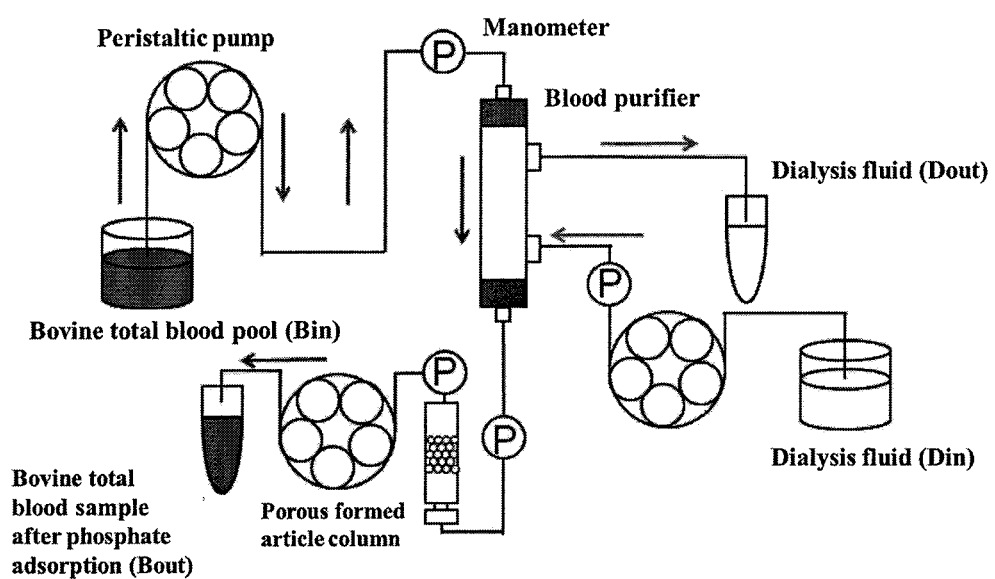
FIG. 10 is a schematic diagram showing circuit 3 for the measurement test of the amount of phosphate removed in Production Example 16 and Comparative Example 4.
Figure 11:
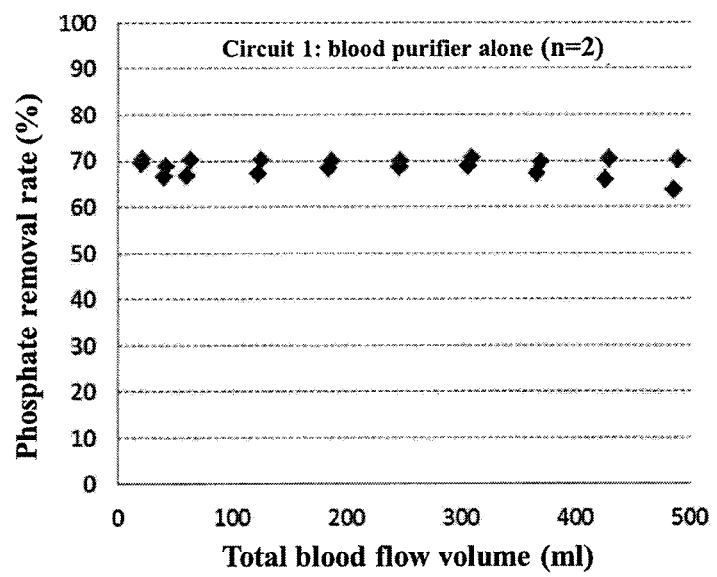
FIG. 11 shows the relationship between a phosphate removal rate and a total blood flow volume in circuit 1.
Figure 12:
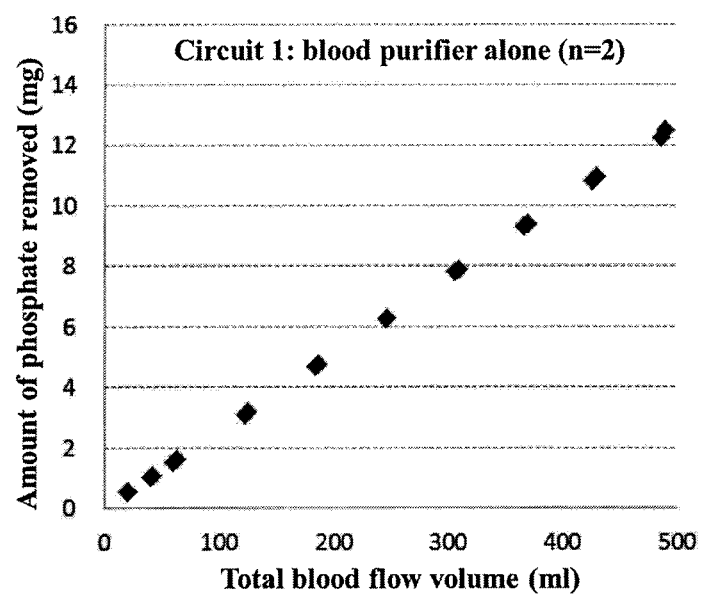
FIG. 12 shows the relationship between the amount of phosphate removed and a total blood flow volume in circuit 1.
Figure 13:
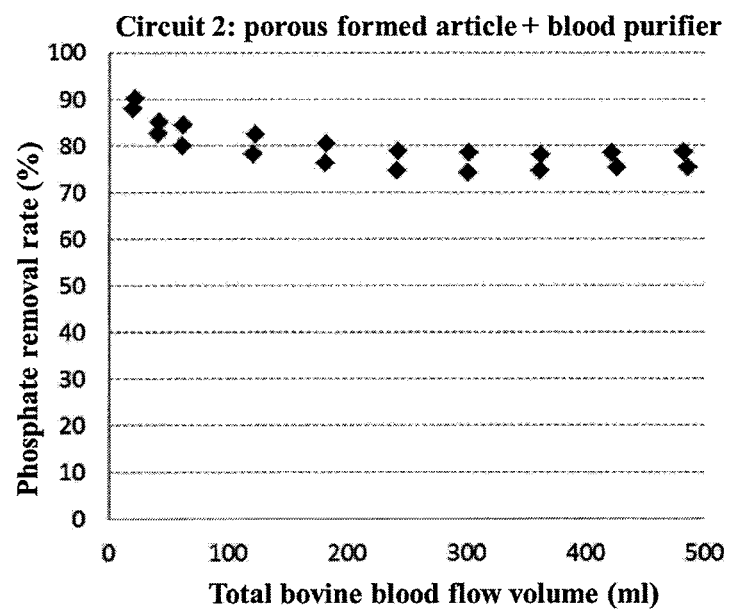
FIG. 13 shows the relationship between a phosphate removal rate and a total blood flow volume in circuit 2 in the case of using a column packed with a spherical porous formed article prepared in Production Example 8 (phosphate adsorbing agent for blood processing).
Figure 14:
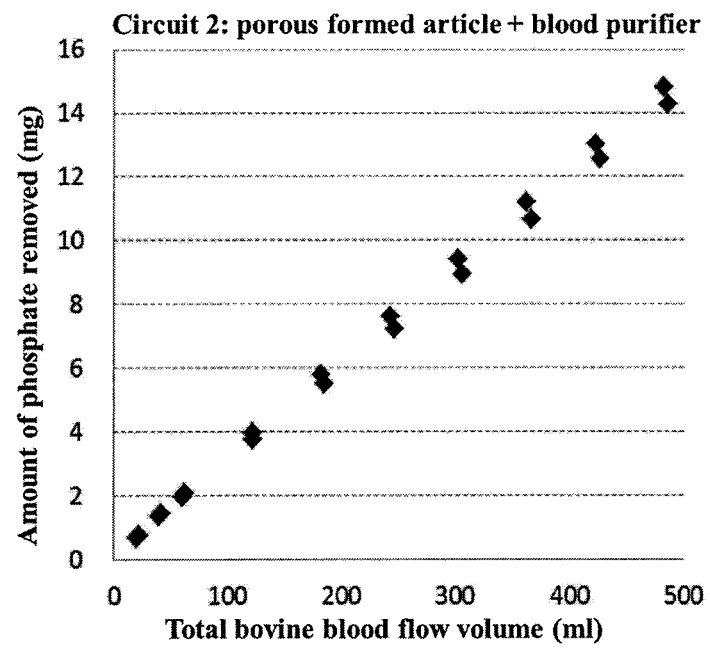
FIG. 14 shows the relationship between the amount of phosphate removed and a total blood flow volume in circuit 2 in the case of using the column packed with the spherical porous formed article prepared in Production Example 8 (phosphate adsorbing agent for blood processing).
Figure 15:
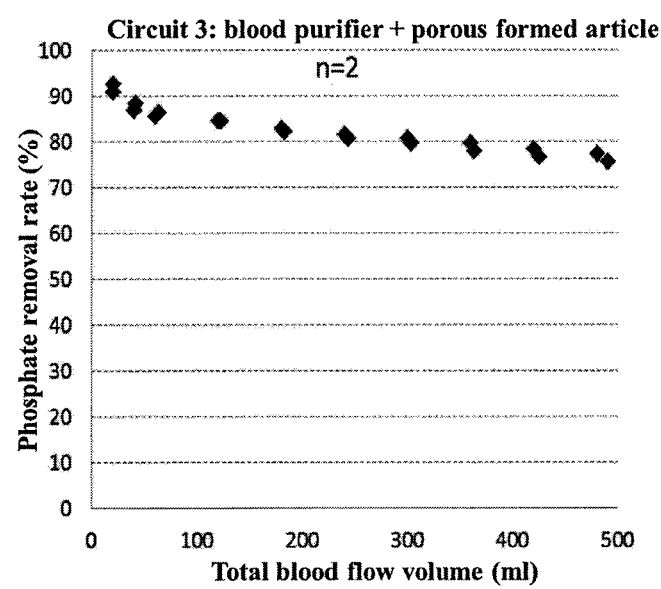
FIG. 15 shows the relationship between a phosphate removal rate and a total blood flow volume in circuit 3 in the case of using the column packed with the spherical porous formed article prepared in Production Example 8 (phosphate adsorbing agent for blood processing).
Figure 16:
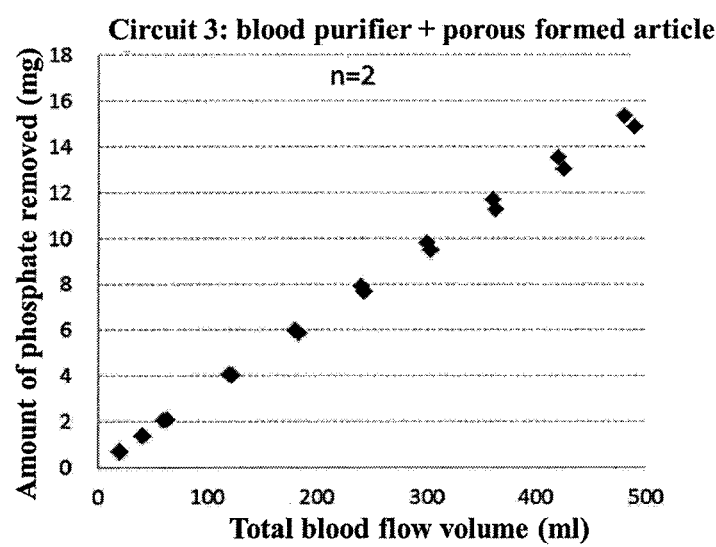
FIG. 16 shows the relationship between the amount of phosphate removed and a total blood flow volume in circuit 3 in the case of using the column packed with the spherical porous formed article prepared in Production Example 8 (phosphate adsorbing agent for blood processing).

In Production Example 16, the amount of phosphate removed was measured in circuit 2 (FIG. 9) and circuit 3 (FIG. 10) using the blood processor and a column packed with the spherical porous formed article prepared in Production Example 8 (phosphate adsorbing agent for blood processing).

In Comparative Example 4, the amount of phosphate removed was measured in circuit 2 and circuit 3 using a column packed with the spherical porous formed article prepared in Comparative Example 2 instead of the column packed with the spherical porous formed article prepared in Production Example 8.

The results are shown in Tables 4 to 8 and FIGS. 11 to 16. The results obtained in circuit 1 are shown.

TABLE 4

Blood purifier alone (n = 2)

| Sample No. | Total blood flow time (min) | Total blood flow volume (mL) | Phosphate removal rate (%) 1 | 2 | Total amount of phosphate removed (mg) 1 | 2 |
|---|---|---|---|---|---|---|
| 1 | 10 | 20 | 69 | 70 | 0.52 | 0.54 |
| 2 | 20 | 40 | 66 | 69 | 1.02 | 1.06 |
| 3 | 30 | 60 | 67 | 70 | 1.52 | 1.60 |
| 4 | 60 | 120 | 67 | 70 | 3.08 | 3.18 |
| 5 | 90 | 180 | 68 | 70 | 4.67 | 4.76 |
| 6 | 120 | 240 | 69 | 70 | 6.26 | 6.28 |
| 7 | 150 | 300 | 69 | 71 | 7.81 | 7.87 |
| 8 | 180 | 360 | 67 | 70 | 9.32 | 9.39 |
| 9 | 210 | 420 | 66 | 70 | 10.80 | 10.93 |
| 10 | 240 | 480 | 64 | 70 | 12.23 | 12.46 |
| Average value | — | — | — | — | 12.35 | |

The results obtained in circuit 2 using the column packed with the spherical porous formed article prepared in Production Example 8 (phosphate adsorbing agent for blood processing) are shown.

TABLE 5

Porous formed body (Production Example 8) + blood purifier (n = 2)

| Sample No. | Total blood flow time (min) | Total blood flow volume (mL) | Phosphate removal rate (%) 1 | 2 | Total amount of phosphate removed (mg) 1 | 2 |
|---|---|---|---|---|---|---|
| 1 | 10 | 20 | 88 | 90 | 0.68 | 0.76 |
| 2 | 20 | 40 | 83 | 85 | 1.34 | 1.41 |
| 3 | 30 | 60 | 80 | 84 | 1.96 | 2.06 |
| 4 | 60 | 120 | 78 | 82 | 3.76 | 3.95 |
| 5 | 90 | 180 | 76 | 80 | 5.52 | 5.80 |
| 6 | 120 | 240 | 75 | 79 | 7.24 | 7.61 |
| 7 | 150 | 300 | 74 | 78 | 8.95 | 9.41 |
| 8 | 180 | 360 | 75 | 78 | 10.67 | 11.20 |
| 9 | 210 | 420 | 75 | 78 | 12.55 | 13.00 |
| 10 | 240 | 480 | 75 | 79 | 14.28 | 14.81 |
| Average value | | | | | 14.55 | |

The results obtained in circuit 3 using the column packed with the spherical porous formed article prepared in Production Example 8 (phosphate adsorbing agent for blood processing) are shown.

TABLE 6

Blood purifier + porous formed body (Production Example 8) (n = 2)

| Sample No. | Total blood flow time (min) | Total blood flow volume (mL) | Phosphate removal rate (%) 1 | 2 | Total amount of phosphate removed (mg) 1 | 2 |
|---|---|---|---|---|---|---|
| 1 | 10 | 20 | 92 | 91 | 0.69 | 0.71 |
| 2 | 20 | 40 | 88 | 87 | 1.39 | 1.39 |

TABLE 6-continued

Blood purifier + porous formed body (Production Example 8) (n = 2)

| Sample No. | Total blood flow time (min) | Total blood flow volume (mL) | Phosphate removal rate (%) 1 | 2 | Total amount of phosphate removed (mg) 1 | 2 |
|---|---|---|---|---|---|---|
| 3 | 30 | 60 | 86 | 86 | 2.11 | 2.06 |
| 4 | 60 | 120 | 84 | 84 | 4.01 | 4.04 |
| 5 | 90 | 180 | 82 | 83 | 5.86 | 5.99 |
| 6 | 120 | 240 | 81 | 81 | 7.68 | 7.90 |
| 7 | 150 | 300 | 80 | 81 | 9.48 | 9.79 |
| 8 | 180 | 360 | 78 | 80 | 11.23 | 11.66 |
| 9 | 210 | 420 | 77 | 78 | 13.02 | 13.50 |
| 10 | 240 | 480 | 75 | 77 | 14.86 | 15.32 |
| Average value | — | — | — | — | 15.09 | |

The results obtained in circuit 2 using the column packed with the spherical porous formed article prepared in Comparative Example 2 (phosphate adsorbing agent for blood processing) are shown.

TABLE 7

Blood purifier + porous formed body (n = 1)

| Sample No. | Total blood flow time (min) | Total blood flow volume (mL) | Phosphate removal rate (%) | Total amount of phosphate removed (mg) |
|---|---|---|---|---|
| 1 | 10 | 20 | 75 | 0.58 |
| 2 | 20 | 40 | 73 | 1.16 |
| 3 | 30 | 60 | 72 | 1.72 |
| 4 | 60 | 120 | 71 | 3.35 |
| 5 | 90 | 180 | 71 | 4.98 |
| 6 | 120 | 240 | 70 | 6.60 |
| 7 | 150 | 300 | 70 | 8.21 |
| 8 | 180 | 360 | 69 | 9.81 |
| 9 | 210 | 420 | 69 | 11.53 |
| 10 | 240 | 480 | 69 | 13.11 |

The results obtained in circuit 3 using the column packed with the spherical porous formed article prepared in Comparative Example 2 (phosphate adsorbing agent for blood processing) are shown.

TABLE 8

Blood purifier + porous formed body (n = 1)

| Sample No. | Total blood flow time (min) | Total blood flow volume (mL) | Phosphate removal rate (%) | Total amount of phosphate removed (mg) |
|---|---|---|---|---|
| 1 | 10 | 20 | 75 | 0.57 |
| 2 | 20 | 40 | 73 | 1.14 |
| 3 | 30 | 60 | 72 | 1.73 |
| 4 | 60 | 120 | 71 | 3.33 |
| 5 | 90 | 180 | 70 | 4.91 |
| 6 | 120 | 240 | 69 | 6.48 |
| 7 | 150 | 300 | 69 | 8.04 |
| 8 | 180 | 360 | 69 | 9.60 |
| 9 | 210 | 420 | 69 | 11.19 |
| 10 | 240 | 480 | 68 | 12.86 |

In all the cases, experimental conditions and bovine blood preparation were as follows:

Experimental Conditions

Blood purifier: 0.02 m² membrane (effective length: approximately 85 mm, the number of hollow fibers: 420)
Amount of the porous formed article: 0.5 mL column
Total bovine blood flow rate: 2 ml/min
Dialysis fluid flow rate: 5 ml/min
[Blood Preparation]
Ht: 32% (hematocrit: numerical value indicating the volume ratio of blood cells to blood)
TP: 6.027 g/dL (protein concentration)
IP: 4.99 mg/dL (inorganic phosphate concentration)
[Amount (Mg) of Phosphate Removed]
Sampling was performed at a blood outlet and dialysis fluid outlet up to a flow volume 480 mL for 240 minutes after the start of bovine total blood flow from a blood pool, and the phosphate removal rate (%) and the amount (mg) of phosphate removed were measured.
The amount of phosphate removed was compared when the flow volume reached 480 mL.

Amount of phosphate removed with the blood purifier alone=$D$out concentration×Amount sampled Amount of phosphate removed with (Blood purifier+ Porous formed article column) connection=($B$in concentration−$B$out concentration)×(Amount sampled)×(100−$Ht$)/100

For the sake of convenience of sampling, the sampling position was changed for measurement, depending on the presence or absence of the porous formed article column. However, it was confirmed that values were constant among all of the measurement methods.
[Phosphate Removal Rate (%)]

Removal rate (%)=100×($B$in concentration−$B$out concentration)/($B$in concentration)

[Sampling]
The initial concentration was sampled from the blood pool, and the blood outlet concentration ($B$out) and the dialysis fluid outlet concentration ($D$out) were sampled at 10 minutes, 20 minutes, 30 minutes, 60 minutes and 90 minutes after the start of flow, and subsequently every 30 minutes up to 240 minutes.
The results are summarized in Table 9.

TABLE 9

| Circuit | Content | Total amount of phosphate removed (mg) | |
|---|---|---|---|
| | | Production Example 16 | Comparative Example 4 |
| 1 | Blood purifier alone | 12.35 | 12.35 |
| 2 | Porous formed body + blood purifier | 14.55 | 13.11 |
| 3 | Blood purifier + porous formed body | 15.09 | 12.86 |

The phosphate adsorbing agent for blood processing of the present invention disposed upstream or downstream of the blood purifier was confirmed to drastically increase the amount of phosphate removed.

Example 1 and Comparative Control Example 1

Figure 17:
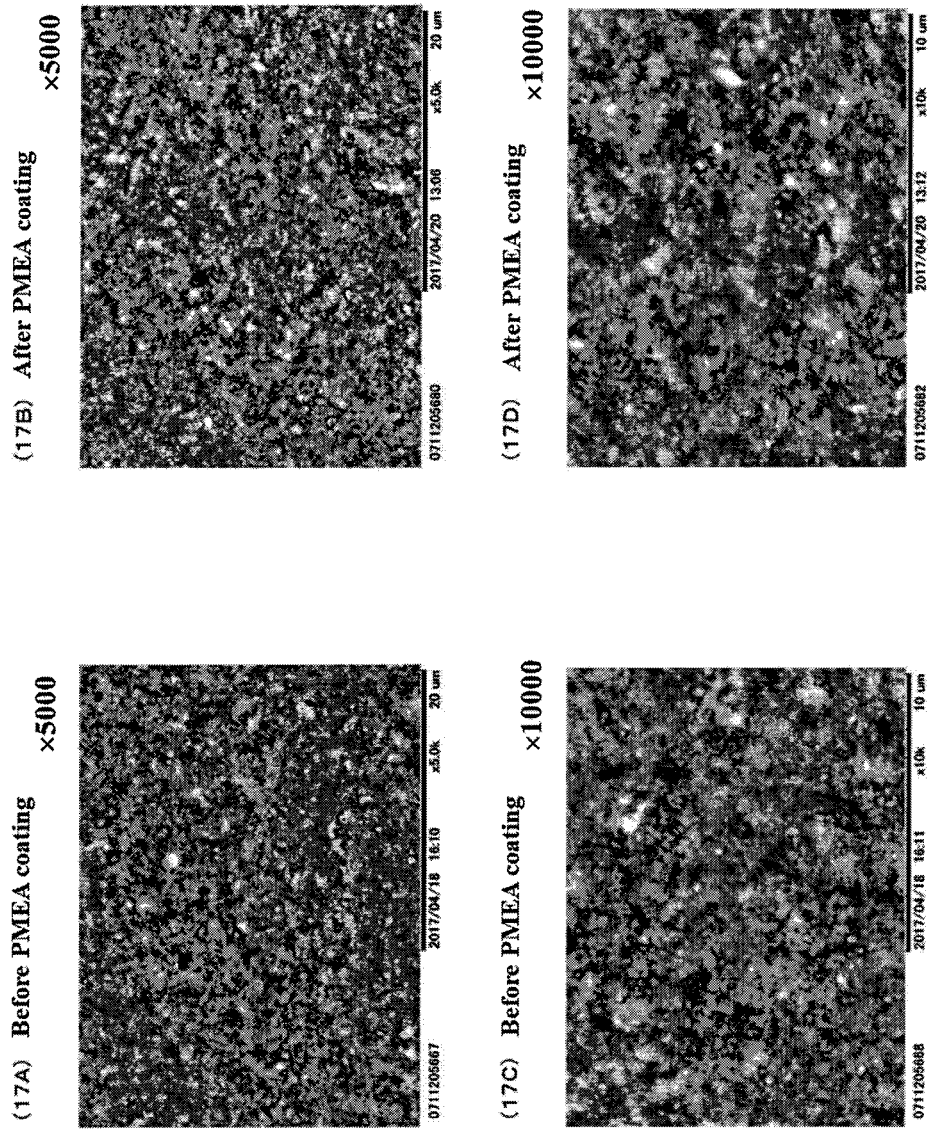
FIG. 17 shows electron microscope photographs (magnification: ×5,000 and ×10,000) showing the surface of porous formed articles prepared in Example 1 and Comparative Control Example 1.

[Preparation of Porous Formed Article]
110 g of N-methyl-2-pyrrolidone (NMP, Mitsubishi Chemical Corp.) and 150 g of a hydrous cerium oxide powder having an average particle size of 30 μm (Konan Muki Co., Ltd.) were added to a stainless ball mill pot (capacity: 1 L) packed with 1.5 kg of stainless balls having a diameter of 5 mmϕ, and subjected to crushing and mixing treatment at 75 rpm for 150 minutes to obtain yellow slurry. To the obtained slurry, 10 g of polyethersulfone (Sumitomo Chemical Co., Ltd., Sumikaexcel 5003PS (trade name), OH-terminated grade, terminal hydroxy group composition: 90 (% by mol)) was added, and the mixture was warmed to 60° C. in a dissolution vessel and dissolved with agitation using an agitation blade to obtain a homogeneous slurry solution for shape forming.
The obtained slurry solution for shape forming was warmed to 60° C. and supplied to the inside of a cylindrical rotary container in which a nozzle having a diameter of 4 mm was opened on the lateral side. This container was rotated to form liquid drops from the nozzle by centrifugal force (15 G). Subsequently, the spatial portion between the rotary container and a coagulation vessel was covered with a polypropylene cover to control the temperature and relative humidity of the spatial portion to 50° C. and 100%, respectively. The liquid drops were allowed to travel in this spatial portion and arrive at a coagulating liquid (content of NMP with respect to water: 50% by mass) warmed to 80° C., which was retained in a coagulation vessel having an upper opening, to coagulate the slurry for shape forming.
Washing and classification were further performed to obtain a spherical porous formed article.
Table 10 shows the physical properties of the obtained porous formed article. Neither the average particle size nor the outer surface opening ratio was changed between before and after PMEA coating. FIG. 17 (FIGS. 17A and 17C) shows electron microscope photographs (magnification: ×5,000 and ×10,000) showing the surface of the obtained porous formed article.

TABLE 10

| Physical properties | Example 1 | Comparative Control Example 1 | Example 2 | Comparative Control Example 2 | Example 3 | Comparative Control Example 3 |
|---|---|---|---|---|---|---|
| Organic polymer resin | PES | PES | PAN | PAN | EVOH | EVQH |
| Presence or absence of PMEA coating | Present | Absent | Present | Absent | Present | Absent |
| Inorganic ion adsorbent | c | c | c | c | c | c |
| Presence or absence of cover used for spatial portion | Present | Present | Present | Present | Present | Present |

TABLE 10-continued

| | | | | | | |
|---|---|---|---|---|---|---|
| Relative humidity of spatial portion (%) | 100 | 100 | 100 | 100 | 100 | 100 |
| Temperature of spatial portion (° C.) | 50 | 50 | 50 | 50 | 50 | 50 |
| Coagulating liquid temperature (° C.) | 80 | 60 | 80 | 80 | 80 | 80 |
| Coagulating liquid composition (good solvent/water) | 50/50 | 50/50 | 50/50 | 50/50 | 0/100 | 0/100 |
| Average particle size (μm) | 296 | 296 | 346 | 346 | 530 | 530 |
| Outer surface opening ratio (%) | 18 | 18 | 20 | 20 | 27 | 27 |
| Presence or absence of skin layer | Absent | Absent | Absent | Absent | Absent | Absent |
| Most frequent pore size measured with mercury porosimeter (μm) | | 0.12 | | 0.37 | | 0.40 |
| Median size measured with mercury porosimeter (μm) | | 0.12 | | 0.31 | | 0.36 |
| Most frequent pore size/median size ratio | | 1.00 | | 1.19 | | 1.11 |
| Specific surface area measured with mercury porosimeter (m$^2$/cm$^3$) | | 16 | | 22 | | 20 |
| Bulk specific gravity (g/cm$^3$) | | 0.67 | | 0.45 | | 0.62 |
| Amount of phosphate adsorbed (mg/ml-Resin) (in water) after 4 hours | 3.89 | 3.66 | 3.97 | 3.84 | 2.56 | 2.47 |
| Amount of phosphate adsorbed when bovine plasma flow volume reached 350 ml (mg-P-mL-Resin) | 3.10 | 2.93 | 3.06 | 2.89 | 1.95 | 1.90 |

| Physical properties | Example 4 | Comparative Control Example 4 | Example 5 | Comparative Control Example 5 | Example 6 | Comparative Control Example 6 |
|---|---|---|---|---|---|---|
| Organic polymer resin | PES | PES | PES | PES | PES | PES |
| Presence or absence of PMEA coating | Present | Absent | Present | Absent | Present | Absent |
| Inorganic ion adsorbent | c | c | z | z | c | c |
| Presence or absence of cover used for spatial portion | Present | Present | Present | Present | Present | Present |
| Relative humidity of spatial portion (%) | 100 | 100 | 100 | 100 | 100 | 100 |
| Temperature of spatial portion (° C.) | 50 | 50 | 50 | 50 | 50 | 50 |
| Coagulating liquid temperature (° C.) | 80 | 80 | 80 | 80 | 80 | 80 |
| Coagulating liquid composition (good solvent/water) | 0/100 | 0/100 | 0/100 | 0/100 | 0/100 | 0/100 |
| Average particle size (μm) | 600 | 600 | 370 | 370 | 543 | 543 |
| Outer surface opening ratio (%) | 19 | 10 | 18 | 18 | 24 | 24 |
| Presence or absence of skin layer | Absent | Absent | Absent | Absent | Absent | Absent |
| Most frequent pore size measured with mercury porosimeter (μm) | | 0.36 | | 0.35 | | 0.33 |
| Median size measured with mercury porosimeter (μm) | | 0.31 | | 0.31 | | 0.30 |
| Most frequent pore size/median size ratio | | 1.10 | | 1.13 | | 1.09 |
| Specific surface area measured with mercury porosimeter (m$^2$/cm$^3$) | | 12 | | 17 | | 25 |
| Bulk specific gravity (g/cm$^3$) | | 0.36 | | 0.51 | | 0.35 |
| Amount of phosphate adsorbed (mg/ml-Resin) (in water) after 4 hours | 2.52 | 2.38 | 2.37 | 2.22 | 3.61 | 3.42 |
| Amount of phosphate adsorbed when bovine plasma flow volume reached 350 ml (mg-P-mL-Resin) | 1.99 | 1.88 | 1.78 | 1.71 | 2.87 | 2.77 |

C: hydrous cerium oxide
Z: zirconium hydroxide

[PMEA Coating of Porous Formed Article]

A cylindrical column (equipped with a glass filter at the bottom) was packed with 50 mL of the obtained porous formed article. Subsequently, 0.2 g of PMEA (Mn: 20,000, Mw/Mn: 2.4) was dissolved in an aqueous solution (100 g) of 40 g of ethanol and 60 g of water to prepare a coating solution. The column packed with the porous formed article was held in a vertical way, and the coating solution was injected at a flow rate of 100 mL/min from above so that the coating solution was contacted with the porous formed article, followed by washing with pure water.

After the washing with pure water, the coating solution in the module was blown off with air of 0.1 KMpa. The module was placed in a vacuum dryer, dried in vacuum at 35° C. for 15 hours, and sterilized with gamma ray of 25 Kgy in the atmosphere.

This sample was subjected to ATR-infrared spectroscopy before and after the PMEA coating. The infrared absorption curve thereof is shown in FIG. 18.

A PMEA-derived ester group (—O—C=O) peak of infrared absorption (around 1735 cm$^{-1}$) was confirmed.

Table 10 shows the physical properties of the obtained PMEA-coated porous formed article. FIG. 17 (FIGS. 17B and 17D) shows electron microscope photographs (magnification: ×5,000 and ×10,000) showing the surface of the obtained PMEA-coated porous formed article.

[Amount of Phosphate Adsorbed in Water]

The amount of phosphate adsorbed was measured as to the PMEA-coated porous formed article and the uncoated porous formed article by the following method.

Sodium dihydrogen phosphate (NaH$_2$PO$_4$) was dissolved in distilled water to prepare a solution having a phosphate concentration of 9 mg-P/L. Its pH was adjusted to 7 with sodium hydroxide, and the resulting solution was used as an adsorption dope.

A column (inside diameter: 10 mm) was packed with 2 mL of the porous formed article weighed by repeated tapping using a measuring cylinder. The adsorption dope was injected thereto at a fluid flow rate of 240 mL/hr (SV120).

An effluent (processed fluid) from the column was sampled every 10 minutes, and the phosphate concentration of the processed water was measured to determine the cumulative amount of phosphate adsorbed (amount adsorbed: mg-P/mL-Resin) up to 4 hours later.

FIG. 19 shows results of measuring the phosphate ion concentration over time using a phosphate measurement apparatus Phosphax Compact (trade name) manufactured by HACH Company. FIG. 20 shows the cumulative amount adsorbed. The results are also shown in Table 11.

TABLE 11

| Elapsed time [hr] | BV | Before PMEA coating | | After PMEA coating | |
|---|---|---|---|---|---|
| | | Outlet phosphate concentration [mg/L] | Cumulative amount adsorbed [mg-P/mL-Resin] | Outlet phosphate concentration [mg/L] | Cumulative amount adsorbed [mg-P/mL-Resin] |
| 0.00 | 0 | 0.000 | 0.000 | 0.000 | 0.000 |
| 0.17 | 20 | 0.000 | 0.179 | 0.000 | 0.179 |
| 0.33 | 40 | 0.000 | 0.357 | 0.000 | 0.357 |
| 0.50 | 60 | 0.000 | 0.536 | 0.000 | 0.536 |
| 0.67 | 80 | 0.000 | 0.715 | 0.000 | 0.715 |
| 0.83 | 100 | 0.000 | 0.893 | 0.000 | 0.893 |
| 1.00 | 120 | 0.000 | 1.072 | 0.000 | 1.072 |
| 1.17 | 140 | 0.000 | 1.251 | 0.000 | 1.251 |
| 1.33 | 160 | 0.071 | 1.429 | 0.000 | 1.429 |
| 1.50 | 180 | 0.195 | 1.605 | 0.000 | 1.608 |
| 1.67 | 200 | 0.318 | 1.778 | 0.000 | 1.787 |
| 1.83 | 220 | 0.522 | 1.948 | 0.092 | 1.964 |
| 2.00 | 240 | 0.811 | 2.114 | 0.229 | 2.140 |
| 2.17 | 260 | 1.001 | 2.274 | 0.444 | 2.312 |
| 2.33 | 280 | 1.277 | 2.430 | 0.751 | 2.479 |
| 2.50 | 300 | 1.568 | 2.580 | 1.052 | 2.639 |
| 2.67 | 320 | 1.896 | 2.725 | 1.356 | 2.794 |
| 2.83 | 340 | 2.324 | 2.861 | 1.620 | 2.943 |
| 3.00 | 360 | 2.590 | 2.991 | 1.838 | 3.087 |
| 3.17 | 380 | 2.926 | 3.114 | 2.008 | 3.227 |
| 3.33 | 400 | 3.219 | 3.231 | 2.162 | 3.364 |
| 3.50 | 420 | 3.436 | 3.343 | 2.297 | 3.498 |
| 3.67 | 440 | 3.572 | 3.452 | 2.418 | 3.630 |
| 3.83 | 460 | 3.705 | 3.558 | 2.527 | 3.759 |
| 4.00 | 480 | 3.795 | 3.662 | 2.639 | 3.886 |

The amount of phosphate adsorbed after 4 hours was 3.662 mg-P/mL-Resin for the PMEA-uncoated sample, whereas this amount was 3.886 mg-P/mL-Resin for the PMEA-coated sample and was thus increased in the PMEA-coated sample.

(Column Flow Test Using Low-Phosphate Concentration Serum from Bovine Plasma)

The inorganic phosphate concentration in blood at the outlet of a dialyzer at the time of dialysis treatment was 0.2 to 1.0 mg/dL. Therefore, the amount of phosphate adsorbed in this concentration range must be measured. Therefore, the phosphate concentration of a test plasma fluid was adjusted.

Commercially available bovine serum was centrifuged (3500 rpm, 5 min) to prepare 2000 mL of a supernatant plasma. The phosphate concentration in the plasma was 10.8 mg/dL.

To half (1000 mL) the amount of the obtained plasma, the porous formed article obtained in Example 1 was added, and the mixture was agitated at room temperature for 2 hours and centrifuged (3500 rpm, 5 min) to obtain approximately 950 mL of plasma having a phosphate concentration of 0.

33 mL of the plasma having a phosphate concentration of 10.8 mg/dL and 467 mL of the plasma having a phosphate concentration of 0 were mixed and centrifuged (3500 rpm, 5 min) to obtain 495 mL of plasma having a phosphate concentration of 0.9 mg/dL as a supernatant.

A column packed with 1 mL of the porous formed article was assembled according to the schematic diagram shown in FIG. 5. 450 mL of the obtained plasma was injected thereto at a flow rate of 2 mL/min. 10 mL was collected for the first fraction, and 20 mL/sample was collected for subsequent fractions. Average dialysis conditions typically involve performing dialysis at flow rate Qb=200 mL/min for 4 hours. Therefore, 200 mL×4 hours=48000 mL is obtained as a total blood flow volume. When blood cell components have Ht=30%, the flow volume of plasma is 33600 mL. Since this experiment was conducted on a scale of 1/100, fluid flow of 350 mL was used as a guideline.

Tables 12 and 13 show the plasma flow volume, the column-outlet phosphate concentration, the phosphate adsorption rate (%) and the total amount adsorbed before and after PMEA coating.

Before PMEA Coating

TABLE 12

| Fraction No. | Plasma flow volume (mL) | Outlet phosphate concentration (mg/dL) | Phosphate adsorption rate (%) | Total amount adsorbed (mg-P/mL-Resin) |
|---|---|---|---|---|
| 1 | 10 | 0 | 100 | 0.09 |
| 2 | 30 | 0 | 100 | 0.27 |
| 3 | 50 | 0 | 100 | 0.45 |
| 4 | 70 | 0 | 100 | 0.63 |
| 5 | 90 | 0.05 | 100 | 0.80 |
| 6 | 110 | 0.05 | 100 | 0.97 |
| 7 | 130 | 0.05 | 94.5 | 1.14 |
| 8 | 150 | 0.05 | 94.5 | 1.31 |
| 9 | 170 | 0.05 | 94.5 | 1.48 |
| 10 | 190 | 0.05 | 94.5 | 1.65 |
| 11 | 210 | 0.10 | 89 | 1.81 |
| 12 | 230 | 0.10 | 89 | 1.97 |
| 13 | 250 | 0.10 | 89 | 2.13 |
| 14 | 270 | 0.10 | 89 | 2.29 |
| 15 | 290 | 0.10 | 89 | 2.45 |
| 16 | 310 | 0.10 | 89 | 2.61 |
| 17 | 330 | 0.10 | 89 | 2.77 |
| 18 | 350 | 0.10 | 89 | 2.93 |

After PMEA Coating

TABLE 13

| Fraction No. | Plasma flow volume (mL) | Outlet phosphate concentration (mg/dL) | Phosphate adsorption rate (%) | Total amount adsorbed (mg-P/mL-Resin) |
|---|---|---|---|---|
| 1 | 10 | 0 | 100 | 0.09 |
| 2 | 30 | 0 | 100 | 0.27 |

TABLE 13-continued

| Fraction No. | Plasma flow volume (mL) | Outlet phosphate concentration (mg/dL) | Phosphate adsorption rate (%) | Total amount adsorbed (mg-P/mL-Resin) |
|---|---|---|---|---|
| 3 | 50 | 0 | 100 | 0.45 |
| 4 | 70 | 0 | 100 | 0.63 |
| 5 | 90 | 0 | 100 | 0.81 |
| 6 | 110 | 0 | 100 | 0.99 |
| 7 | 130 | 0 | 100 | 1.17 |
| 8 | 150 | 0 | 100 | 1.35 |
| 9 | 170 | 0 | 100 | 1.53 |
| 10 | 190 | 0 | 100 | 1.71 |
| 11 | 210 | 0 | 100 | 1.89 |
| 12 | 230 | 0 | 100 | 2.07 |
| 13 | 250 | 0 | 100 | 2.25 |
| 14 | 270 | 0.05 | 94.5 | 2.42 |
| 15 | 290 | 0.05 | 94.5 | 2.59 |
| 16 | 310 | 0.05 | 94.5 | 2.76 |
| 17 | 330 | 0.05 | 94.5 | 2.93 |
| 18 | 350 | 0.05 | 94.5 | 3.10 |

The amount of phosphate adsorbed (mg-P/mL-Resin) when the bovine plasma flow volume reached 350 mL was 3.10 (mg-P/mL-Resin) after the PMEA coating and 2.93 (mg-P/mL-Resin) before the PMEA coating and was thus increased after the PMEA coating.

Earlier elevation in outlet phosphate concentration (breaking through the column) was seen before the PMEA coating than after the PMEA coating
(Measurement of White Blood Cell and Platelet)

Next, the PMEA-coated sample and the uncoated sample of the porous formed article were evaluated for their white blood cell and platelet adsorbing properties.

An apparatus is assembled as shown in FIG. 5. The column is packed with 0.5 mL of the phosphate adsorbing agent. 15 mL of human blood is provided, and heparin is added thereto at a ratio of 7 units/mL. The resulting human blood was sent at a blood flow rate of 1 mL/min (space velocity SV=120) into the column using a peristaltic pump. The first 5-mL flow of blood coming out of the column was eliminated, and the subsequent 5-ml flow of blood was then measured using a multi-item automatic blood cell analysis apparatus XT-1800i.

The white blood cell recovery rate (%) was 94% before the PMEA coating and 95% after the PMEA coating.

The platelet recovery rate (%) was 64% before the PMEA coating and 75% after the PMEA coating. Thus, the recovery rates were improved by the coating with PMEA.

TABLE 14

| | White blood cell recovery rate (%) | Platelet recovery rate (%) |
|---|---|---|
| Example 1 | 95 | 75 |
| Comparative Control Example 1 | 94 | 64 |

Example 2 and Comparative Control Example 2

A spherical porous formed article was obtained in the same way as the method described in Example 1 except that: the organic polymer resin was changed to 5 g of a copolymer consisting of 91.5% by mass of acrylonitrile, 8.0% by mass of methyl acrylate and 0.5% by mass of sodium methallylsulfonate and having limiting viscosity [η]=1.2 (organic polymer resin, PAN); and 2 g of polyvinylpyrrolidone (PVP, BASF Japan Ltd., Luvitec K30 Powder (trade name)) was further added as the water-soluble polymer.

Table 10 shows the physical properties of the obtained porous formed article.

The amount of phosphate adsorbed (mg-P/mL-Resin) after 4 hours, the amount of phosphate adsorbed (mg-P/mL-Resin) when the bovine plasma flow volume reached 350 mL, the white blood cell recovery rate (%), and the platelet recovery rate were measured with and without PMEA coating in the same way as in Example 1 and Comparative Control Example 1.

TABLE 15

| | Amount of phosphate adsorbed (mg-P/mL-Resin) (in water) after 4 hours | Amount of phosphate adsorbed (mg-P/mL-Resin) when bovine plasma flow volume reached 350 mL | White blood cell recovery rate (%) | Platelet recovery rate (%) |
|---|---|---|---|---|
| Example 2 | 3.97 | 3.06 | 96 | 78 |
| Comparative Control Example 2 | 3.84 | 2.89 | 94 | 66 |

The detailed amount of phosphate adsorbed in processed water is shown in Table 16 and FIGS. 21 and 22.

TABLE 16

| | | Before PMEA coating | | After PMEA coating | |
|---|---|---|---|---|---|
| Elapsed time [hr] | BV | Outlet phosphate concentration [mg/L] | Cumulative amount adsorbed [mg-P/mL-Resin] | Outlet phosphate concentration [mg/L] | Cumulative amount adsorbed [mg-P/mL-Resin] |
| 0.00 | 0 | 0.000 | 0.000 | 0.000 | 0.000 |
| 0.17 | 20 | 0.000 | 0.176 | 0.000 | 0.178 |
| 0.33 | 40 | 0.000 | 0.352 | 0.000 | 0.355 |
| 0.50 | 60 | 0.000 | 0.528 | 0.000 | 0.533 |
| 0.67 | 80 | 0.000 | 0.704 | 0.000 | 0.710 |
| 0.83 | 100 | 0.000 | 0.880 | 0.000 | 0.888 |
| 1.00 | 120 | 0.000 | 1.056 | 0.006 | 1.066 |
| 1.17 | 140 | 0.000 | 1.232 | 0.039 | 1.243 |
| 1.33 | 160 | 0.062 | 1.407 | 0.095 | 1.419 |
| 1.50 | 180 | 0.142 | 1.581 | 0.148 | 1.594 |
| 1.67 | 200 | 0.221 | 1.754 | 0.222 | 1.768 |
| 1.83 | 220 | 0.313 | 1.924 | 0.285 | 1.941 |
| 2.00 | 240 | 0.407 | 2.093 | 0.361 | 2.112 |
| 2.17 | 260 | 0.440 | 2.261 | 0.439 | 2.282 |
| 2.33 | 280 | 0.529 | 2.427 | 0.514 | 2.450 |

TABLE 16-continued

| | | Before PMEA coating | | After PMEA coating | |
|---|---|---|---|---|---|
| Elapsed time [hr] | BV | Outlet phosphate concentration [mg/L] | Cumulative amount adsorbed [mg-P/mL-Resin] | Outlet phosphate concentration [mg/L] | Cumulative amount adsorbed [mg-P/mL-Resin] |
| 2.50 | 300 | 0.616 | 2.592 | 0.602 | 2.616 |
| 2.67 | 320 | 0.737 | 2.754 | 0.685 | 2.781 |
| 2.83 | 340 | 0.866 | 2.914 | 0.769 | 2.944 |
| 3.00 | 360 | 0.995 | 3.071 | 0.852 | 3.105 |
| 3.17 | 380 | 1.106 | 3.226 | 0.938 | 3.265 |
| 3.33 | 400 | 1.213 | 3.379 | 1.027 | 3.423 |
| 3.50 | 420 | 1.328 | 3.530 | 1.120 | 3.579 |
| 3.67 | 440 | 1.475 | 3.678 | 1.194 | 3.734 |
| 3.83 | 460 | 1.577 | 3.823 | 1.284 | 3.886 |
| 4.00 | 480 | 1.692 | 3.967 | 1.385 | 4.037 |

Example 3 and Comparative Control Example 3

A spherical porous formed article was obtained in the same way as the method described in Example 1 except that: the good solvent for the organic polymer resin was changed to 160 g of dimethyl sulfoxide (DMSO, Kanto Chemical Co., Inc.); the organic polymer resin was changed to 20 g of an ethylene vinyl alcohol copolymer (EVOH, The Nippon Synthetic Chemical Industry Co., Ltd., Soarnol E3803 (trade name)); the amount of the hydrous cerium oxide powder added was set to 250 g; the coagulating liquid was water; and the nozzle diameter was 5 mm.

Table 10 shows the physical properties of the obtained porous formed article.

The amount of phosphate adsorbed (mg-P/mL-Resin) after 4 hours, the amount of phosphate adsorbed (mg-P/mL-Resin) when the bovine plasma flow volume reached 350 mL, the white blood cell recovery rate (%), and the platelet recovery rate were measured with and without PMEA coating in the same way as in Example 1 and Comparative Control Example 1.

TABLE 17

| | Amount of phosphate adsorbed (mg-P/mL-Resin) after 4 hours | Amount of phosphate adsorbed (mg-P/mL-Resin) when bovine plasma flow volume reached 350 mL | White blood cell recovery rate (%) | Platelet recovery rate (%) |
|---|---|---|---|---|
| Example 3 | 2.56 | 1.95 | 96 | 79 |
| Comparative Control Example 3 | 2.47 | 1.90 | 96 | 64 |

Example 4 and Comparative Control Example 4

A spherical porous formed article was obtained in the same way as the method described in Example 1 except that: the amount of polyethersulfone (Sumitomo Chemical Co., Ltd., Sumikaexcel 5003PS (trade name), OH-terminated grade, terminal hydroxy group composition: 90 (% by mol)) added was increased to 15 g; 2 g of polyethylene glycol (PEG35,000, Merck Japan) was added as the water-soluble polymer; the coagulating liquid was water; and the nozzle diameter was 5 mm.

Table 10 shows the physical properties of the obtained porous formed article.

The amount of phosphate adsorbed (mg-P/mL-Resin) after 4 hours, the amount of phosphate adsorbed (mg-P/mL-Resin) when the bovine plasma flow volume reached 350 mL, the white blood cell recovery rate (%), and the platelet recovery rate were measured with and without PMEA coating in the same way as in Example 1 and Comparative Control Example 1.

TABLE 18

| | Amount of phosphate adsorbed (mg-P/mL-Resin) after 4 hours | Amount of phosphate adsorbed (mg-P/mL-Resin) when bovine plasma flow volume reached 350 mL | White blood cell recovery rate (%) | Platelet recovery rate (%) |
|---|---|---|---|---|
| Example 4 | 2.52 | 1.99 | 96 | 79 |
| Comparative Control Example 4 | 2.38 | 1.88 | 95 | 64 |

Example 5 and Comparative Control Example 5

A spherical porous formed article was obtained in the same way as the method described in Example 1 except that: the inorganic ion adsorbent used was a hydrous zirconium oxide powder (Daiichi Kigenso Kagaku Kogyo Co., Ltd., R Zirconium Hydroxide (trade name)) dried with a constant mass in a dryer of 70° C.; the amount of polyethersulfone (Sumitomo Chemical Co., Ltd., Sumikaexcel 5003PS (trade name), OH-terminated grade, terminal hydroxy group composition: 90 (% by mol)) added was increased to 15 g; 2 g of polyethylene glycol (PEG35,000, Merck Japan) was added as the water-soluble polymer; and the coagulating liquid was water.

Table 10 shows the physical properties of the obtained porous formed article.

The amount of phosphate adsorbed (mg-P/mL-Resin) after 4 hours, the amount of phosphate adsorbed (mg-P/mL-Resin) when the bovine plasma flow volume reached 350 mL, the white blood cell recovery rate (%), and the platelet recovery rate were measured with and without PMEA coating in the same way as in Example 1 and Comparative Control Example 1.

TABLE 19

|  | Amount of phosphate adsorbed (mg-P/mL-Resin) after 4 hours | Amount of phosphate adsorbed (mg-P/mL-Resin) when bovine plasma flow volume reached 350 mL | White blood cell recovery rate (%) | Platelet recovery rate (%) |
|---|---|---|---|---|
| Example 5 | 2.37 | 1.78 | 95 | 79 |
| Comparative Control Example 5 | 2.22 | 1.71 | 95 | 68 |

Example 6 and Comparative Control Example 6

147 g of NMP and 80.5 g of a hydrous cerium oxide powder having an average particle size of 30 μm (Konan Muki Co., Ltd.) were added to a stainless ball mill pot (capacity: 1 L) packed with 1.5 kg of stainless balls having a diameter of 5 mmφ, and subjected to crushing and mixing treatment at 75 rpm for 200 minutes to obtain yellow slurry. A spherical porous formed article was obtained in the same way as the method described in Example 1 except that: to the obtained slurry, 21.3 g of polyethersulfone (Sumitomo Chemical Co., Ltd., Sumikaexcel 5003PS (trade name), OH-terminated grade, terminal hydroxy group composition: 90 (% by mol)), and 21.3 g of polyvinylpyrrolidone (PVP, BASF Japan Ltd.) as the water-soluble polymer were added; the coagulating liquid was water; and the nozzle diameter was 5 mm.

Table 10 shows the physical properties of the obtained porous formed article.

(Blood Compatibility Evaluation Using Human Blood)

A sample coated with PMEA according to the procedures was used in Example. A PMEA-uncoated sample was used as a positive control (Comparative Example). The evaluation was conducted by selecting a PMEA-coated sample of the formed article of Example 1 as a negative control.

An experimental circuit was assembled as shown in FIG. 23 and primed with saline at a flow rate of 1 mL/min for 10 minutes. Then, blood collected from a healthy human was injected to the column at a flow rate of 1 mL/min and sampled every 5 minutes (5 mL). The flow test was conducted up to 15 mL, and the white blood cell count (WBC), the red blood cell count (RBC), and the platelet count (PLT) were measured using a multi-item automatic blood cell analysis apparatus (XT-1800i).

The blood thus collected had WBC=$58.6 \times 10^2$/μL, RBC=$435 \times 10^4$/μL, and PLT=$26.4 \times 10^4$/μL. The PMEA-coated product of Example 6 had the highest PLT recovery rate (%) and the smallest change in pressure (KPa) measured in a manometer.

For each sample, the amount of beads was adjusted to 0.5 mL, and the heparin concentration in blood was adjusted to 1.5 U/mL.

The results are shown in Tables 20 to 22 and FIGS. 24 and 25.

Example 6

TABLE 20

| Flow volume [mL] | 0 | 5 | 10 | 15 |
|---|---|---|---|---|
| WBC | 58.6 | 46.5 | 50.4 | 55.3 |
| RBC | 435 | 437 | 449 | 419 |
| PLT | 26.4 | 10.2 | 12.6 | 17.5 |
| WBC recovery rate | 100 | 79% | 86% | 94% |
| RBC recovery rate | 100 | 100% | 103% | 96% |
| PLT recovery rate | 100 | 39% | 48% | 66% |
| Pressure | 1.8 | 3.1 | 4.1 | 4.8 |

Comparative Control Example 6

TABLE 21

| Flow volume [mL] | 0 | 5 | 10 | 15 |
|---|---|---|---|---|
| WBC | 58.6 | 46.6 | 51.5 | 55.2 |
| RBC | 435 | 442 | 442 | 413 |
| PLT | 26.4 | 6 | 6.8 | 9.9 |
| WBC recovery rate | 100 | 80% | 88% | 94% |
| RBC recovery rate | 100 | 102% | 102% | 95% |
| PLT recovery rate | 100 | 23% | 26% | 38% |
| Pressure | 1.8 | 5.5 | 10.2 | 18.6 |

Example 1

TABLE 22

| Flow volume [mL] | 0 | 5 | 10 | 15 |
|---|---|---|---|---|
| WBC | 58.6 | 46.6 | 51.5 | 55.2 |
| RBC | 435 | 442 | 442 | 413 |
| PLT | 26.4 | 10 | 11.5 | 12.7 |
| WBC recovery rate | 100 | 80% | 88% | 94% |
| RBC recovery rate | 100 | 102% | 102% | 95% |
| PLT recovery rate | 100 | 38% | 44% | 48% |
| Pressure | 1.8 | 3.8 | 6.2 | 7.5 |

The present application is based on Japanese Patent Application No. 2017-98444 filed on May 17, 2017, the contents of which are incorporated herein by reference.

INDUSTRIAL APPLICABILITY

The phosphate adsorbing agent for blood processing of the present invention can be preferably used in dialysis therapy and the like and as such, has industrial applicability.

REFERENCE SIGNS LIST

1 Tank
2 Pump
3 Spatial portion cover
4 Coagulation vessel
5 Rotary container
6 Rotary shaft
7 Hose
8 Heater
a Slurry for shape forming
b Opening
c Spatial portion
d Coagulating liquid
11 Thermostat bath
12 Experimental bench
13 Pump
14 Phosphate adsorbing agent-packed column
15 Manometer
16 Sampling

The invention claimed is:

1. A phosphate adsorbing agent for blood processing comprising a porous formed article comprising an organic polymer resin and an inorganic ion adsorbent and having a most frequent pore size of 0.08 to 0.70 μm measured with a mercury porosimeter, the porous formed article comprising a surface,
the phosphate adsorbing agent for blood processing having an ultrathin membrane of a biocompatible polymer in the surface of the porous formed article,
wherein the biocompatible polymer is poly(methoxyethyl acrylate), and
wherein a depth of a superficial layer corresponding to the surface of the porous formed article is equal to the attenuated total reflection-infrared spectroscopy measurement region which is a region within 1 μm from the surface.

2. The phosphate adsorbing agent for blood processing according to claim 1, wherein the phosphate adsorbing agent is configured so that a ratio of an amount of phosphate adsorbed to the phosphate adsorbing agent for blood processing to an amount of phosphate adsorbed to the porous formed article is 1.01 or more.

3. The phosphate adsorbing agent for blood processing according to claim 1, wherein an outer surface opening ratio of the porous formed article is 5% or more and less than 30%.

4. The phosphate adsorbing agent for blood processing according to claim 1, wherein a specific surface area measured with a mercury porosimeter, of the porous formed article is 10 to 100 m$^2$/cm$^3$.

5. The phosphate adsorbing agent for blood processing according to claim 1, wherein a ratio of the most frequent pore size to the median size measured with a mercury porosimeter, of the porous formed article is 0.80 to 1.30.

6. The phosphate adsorbing agent for blood processing according to claim 1, wherein the porous formed article is spherical particles having an average particle size of 100 to 2500 μm.

7. The phosphate adsorbing agent for blood processing according to claim 1, wherein the inorganic ion adsorbent contains at least one metal oxide represented by the following formula (I):

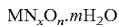 (I)

wherein x is 0 to 3, n is 1 to 4, m is 0 to 6, and M and N are different from each other and each represent a metal element selected from the group consisting of Ti, Zr, Sn, Sc, Y, La, Ce, Pr, Nd, Sm, Eu, Gd, Tb, Dy, Ho, Er, Tm, Yb, Lu, Al, Si, Cr, Co, Ga, Fe, Mn, Ni, V, Ge, Nb and Ta.

8. The phosphate adsorbing agent for blood processing according to claim 7, wherein the metal oxide contains at least one material selected from any of the following groups (a) to (c):
(a) hydrous titanium oxide, hydrous zirconium oxide, hydrous tin oxide, hydrous cerium oxide, hydrous lanthanum oxide and hydrous yttrium oxide,
(b) a mixed metal oxide of at least one metal element selected from the group consisting of titanium, zirconium, tin, cerium, lanthanum and yttrium, and at least one metal element selected from the group consisting of aluminum, silicon and iron, and
(c) activated alumina.

9. The phosphate adsorbing agent for blood processing according to claim 1, wherein the organic polymer resin contains at least one component selected from the group consisting of an ethylene vinyl alcohol copolymer (EVOH), polyacrylonitrile (PAN), polysulfone (PS), polyethersulfone (PES) and polyvinylidene fluoride (PVDF).

10. A blood processing system comprising a phosphate adsorbing agent for blood processing according to claim 1.

11. The blood processing system according to claim 10, further comprising a blood purifier.

12. The blood processing system according to claim 11, wherein the phosphate adsorbing agent for blood processing is disposed such that blood processed by the blood purifier is processed by the phosphate adsorbing agent for blood processing.

13. The blood processing system according to claim 11, wherein the phosphate adsorbing agent for blood processing is disposed such that blood processed by the phosphate adsorbing agent for blood processing is processed by the blood purifier.

14. A blood processing method comprising phosphate adsorption including processing blood using a phosphate adsorbing agent for blood processing according to claim 1.

15. The blood processing method according to claim 14, comprising:
blood purification including processing blood using a blood purifier; and
the phosphate adsorption step before and/or after the blood purification.

* * * * *